US009671166B2

(12) United States Patent
Plavnik et al.

(10) Patent No.: US 9,671,166 B2
(45) Date of Patent: Jun. 6, 2017

(54) ACOUSTIC-ASSISTED HEAT AND MASS TRANSFER DEVICE

(71) Applicant: Heat Technologies, Inc., Atlanta, GA (US)

(72) Inventors: Zinovy Zalman Plavnik, Atlanta, GA (US); Jason Lye, Atlanta, GA (US)

(73) Assignee: Heat Technologies, Inc., Atlanta, GA (US)

( * ) Notice: Subject to any disclaimer, the term of this patent is extended or adjusted under 35 U.S.C. 154(b) by 0 days.

(21) Appl. No.: 14/808,625

(22) Filed: Jul. 24, 2015

(65) Prior Publication Data

US 2016/0025411 A1 Jan. 28, 2016

Related U.S. Application Data

(60) Provisional application No. 62/028,656, filed on Jul. 24, 2014.

(51) Int. Cl.
*F26B 7/00* (2006.01)
*F26B 3/36* (2006.01)
*G10K 15/04* (2006.01)

(52) U.S. Cl.
CPC .................. *F26B 7/00* (2013.01); *F26B 3/36* (2013.01); *G10K 15/04* (2013.01)

(58) Field of Classification Search
CPC ...... F26B 3/00; F26B 5/00; F26B 7/00; F26B 11/00; F26B 19/00
USPC .......... 34/279, 381, 413, 104, 105; 118/203, 118/239; 165/110, 132
See application file for complete search history.

(56) References Cited

U.S. PATENT DOCUMENTS

| | | | |
|---|---|---|---|
| 2,470,202 | A | 4/1956 | Fowle |
| 2,972,196 | A | 2/1961 | Early et al. |
| 3,557,466 | A | 1/1971 | Bodine |
| 3,668,785 | A | 6/1972 | Rodwin |
| 3,694,926 | A | 10/1972 | Rodwin et al. |
| 3,750,306 | A | 8/1973 | Rodwin et al. |
| 4,302,623 | A | 11/1981 | Canfield |
| 4,561,953 | A | 12/1985 | Muralidhara et al. |
| 4,689,895 | A | 9/1987 | Taylor et al. |

(Continued)

FOREIGN PATENT DOCUMENTS

| | | |
|---|---|---|
| CA | 2748263 | 11/2014 |
| DE | 1031264 | 6/1958 |

(Continued)

OTHER PUBLICATIONS

Ultrasoinc and Megasonic Particle Removal by Ahmed A. Busnaina et al, Precision Cleaning '95 Proceedings, pp. 347-360.*

(Continued)

*Primary Examiner* — Stephen M Gravini
(74) *Attorney, Agent, or Firm* — Taylor English Duma LLP

(57) ABSTRACT

An acoustic energy-transfer apparatus including: an acoustic chest, the acoustic chest defining an inner chamber sized to receive a material to be processed; and an acoustic device positioned within the acoustic chest and oriented to direct acoustic energy towards the material to be processed. A method for drying a material, the method including: positioning a material in an acoustic chest including an acoustic device; and directing acoustically energized air from the acoustic device at the material within the acoustic chest.

20 Claims, 20 Drawing Sheets

(56) References Cited

U.S. PATENT DOCUMENTS

| | | | | |
|---|---|---|---|---|
| 4,729,175 | A | 3/1988 | Beard et al. | |
| 4,763,424 | A | 8/1988 | Taylor et al. | |
| 5,105,557 | A | 4/1992 | Vadasz | |
| 5,220,346 | A | 6/1993 | Carreira et al. | |
| 5,396,270 | A | 3/1995 | Gooray et al. | |
| 5,595,349 | A | 1/1997 | Bergstrom et al. | |
| 5,617,887 | A | 4/1997 | Shibano | |
| 5,630,420 | A | 5/1997 | Vaitekunas | |
| 5,631,685 | A | 5/1997 | Gooray et al. | |
| 6,085,437 | A | 7/2000 | Stipp | |
| 6,090,241 | A | 7/2000 | Trokhan et al. | |
| 6,176,184 | B1 | 1/2001 | Mudry | |
| 6,203,151 | B1 | 3/2001 | Ruhe | |
| 6,210,149 | B1 * | 4/2001 | Plavnik | F23C 15/00 431/1 |
| 6,376,145 | B1 | 4/2002 | Meyer | |
| 6,393,719 | B1 | 5/2002 | Stipp | |
| 6,503,580 | B1 | 1/2003 | Ruffa | |
| 6,662,812 | B1 | 12/2003 | Hertz et al. | |
| 6,742,285 | B2 | 6/2004 | Shepard | |
| 6,754,980 | B2 * | 6/2004 | Lauerhaas | H01L 21/67034 134/1 |
| 6,931,205 | B2 | 8/2005 | Atkins | |
| 7,293,567 | B2 | 11/2007 | Hertz et al. | |
| 7,497,301 | B2 | 3/2009 | Cheng et al. | |
| 8,105,526 | B2 | 1/2012 | Stone et al. | |
| 8,756,825 | B2 * | 6/2014 | Priebe | F26B 3/22 118/239 |
| 8,943,706 | B2 * | 2/2015 | Bucks | F26B 5/02 134/102.1 |
| 9,068,775 | B2 | 6/2015 | Plavnik | |
| 9,163,875 | B2 * | 10/2015 | Bucks | B41M 7/0072 |
| 2003/0184630 | A1 | 10/2003 | Elgee | |
| 2004/0011133 | A1 | 1/2004 | Busch et al. | |
| 2007/0169371 | A1 | 7/2007 | Feng et al. | |
| 2007/0169800 | A1 | 7/2007 | Fani et al. | |
| 2008/0301971 | A1 | 12/2008 | Koretsky | |
| 2009/0007931 | A1 | 1/2009 | Krebs et al. | |
| 2009/0300939 | A1 | 12/2009 | Kennedy et al. | |
| 2010/0071194 | A1 | 3/2010 | Derrick et al. | |
| 2010/0199510 | A1 | 8/2010 | Plavnik | |
| 2014/0202021 | A1 * | 7/2014 | Bucks | B41J 11/002 34/279 |
| 2015/0233637 | A1 * | 8/2015 | Plavnik | F26B 3/283 34/426 |
| 2015/0239021 | A1 | 8/2015 | Ponomarev | |
| 2016/0003541 | A1 * | 1/2016 | Plavnik | F26B 5/02 34/401 |
| 2016/0025411 | A1 * | 1/2016 | Plavnik | F26B 7/00 34/279 |

FOREIGN PATENT DOCUMENTS

| | | | |
|---|---|---|---|
| DE | 2053284 | 5/1971 | |
| JP | H05133683 | 5/1993 | |
| JP | 0626764 | 2/1994 | |
| JP | H0626764 | 2/1994 | |
| JP | 2000258055 | 9/2000 | |
| KR | 101273231 B1 * | 6/2013 | D06B 23/16 |
| WO | 9805580 | 2/1998 | |
| WO | 0001883 | 1/2000 | |
| WO | 0019007 | 4/2000 | |
| WO | 0196115 | 12/2001 | |
| WO | 2006042559 | 4/2006 | |
| WO | 2009057054 | 5/2009 | |
| WO | 2010090690 | 12/2010 | |
| WO | 2013182654 | 12/2013 | |
| WO | WO 2014113318 A1 * | 7/2014 | B41M 7/0072 |
| WO | WO 2016014960 A1 * | 1/2016 | F26B 7/00 |

OTHER PUBLICATIONS

Plavnik, Zinovy; International Search Report and Written Opinion for serial No. PCT/US15/42028, filed Jul. 24, 2015, mailed Oct. 23, 2015, 8 pgs.

"PCB Basics" by SFUPTOWNMAKER.. Jan. 12, 2013. Sparkfun. [retrieved from the internet] [retrieved on Aug. 15, 2015]. <URL:https://learn.sparkfun.com/tutorials/pcb-basics> ; p. 4, figure 1, paragraph 1 and 2, 13 pgs.

Plavnik, Zinovy; Advisory Action for U.S. Appl. No. 12/367,803, filed Feb. 9, 2009, mailed Nov. 20, 2012, 6 pgs.

Plavnik, Zinovy; Applicant Initiated Interview Summary for U.S. Appl. No. 12/367,803, filed Feb. 9, 2009, mailed Jan. 28, 2014, 3 pgs.

Plavnik, Zinovy; Applicant Initiated Interview Summary for U.S. Appl. No. 12/367,803, filed Feb. 9, 2009, mailed Jul. 2, 2014, 3 pgs.

Plavnik, Zinovy; Final Office Action for U.S. Appl. No. 12/367,803, filed Feb. 9, 2009, mailed Dec. 2, 2013, 12 pgs.

Plavnik, Zinovy; Final Office Action for U.S. Appl. No. 12/367,803, filed Feb. 9, 2009, mailed Jul. 30, 2012, 21 pgs.

Plavnik, Zinovy; Final Office Action for U.S. Appl. No. 12/367,803, filed Feb. 9, 2009, mailed Nov. 18, 2014, 21 pgs.

Plavnik, Zinovy; Issue Notification for U.S. Appl. No. 12/367,803, filed Feb. 9, 2009, mailed Jun. 10, 2015, 1 pg.

Plavnik, Zinovy; Non-Final Office Action for U.S. Appl. No. 12/367,803, filed Feb. 9, 2009, mailed Jan. 31, 2012, 21 pgs.

Plavnik, Zinovy; Non-Final Office Action for U.S. Appl. No. 12/367,803, filed Feb. 9, 2009, mailed May 1, 2014, 22 pgs.

Plavnik, Zinovy; Non-Final Office Action for U.S. Appl. No. 12/367,803, filed on Feb. 9, 2009, mailed on Apr. 8, 2013, 20 pgs.

Plavnik, Zinovy; Notice of Allowance for U.S. Appl. No. 12/367,803, filed Feb. 9, 2009, mailed Feb. 2, 2015, 11 pgs.

Plavnik, Zinovy; Notice of Allowance for U.S. Appl. No. 12/367,803, filed Feb. 9, 2009, mailed May 18, 2015, 13 pgs.

Plavnik, Zinovy; Restriction Requirement for U.S. Appl. No. 12/367,803, filed Feb. 9, 2009, mailed Oct. 24, 2011, 7 pgs.

Plavnik, Zinovy; U.S. Patent Application entitled: Ultrasonic Drying System and Method, having U.S. Appl. No. 12/367,803, filed Feb. 9, 2009, 60 pgs.

Plavnik, Zinovy; U.S. Continuation Application entitled: Ultrasonic Drying System and Method having U.S. Appl. No. 14/698,104, filed Apr. 28, 2015, 52 pgs.

Plavnik, Zinovy Zalman; U.S. Patent Application entitled: Indirect Acoustic Drying System and Method, U.S. Appl. No. 14/321,354, filed Jul. 1, 2014; 39 pgs.

Plavnik, Zinovy; International Preliminary Report on Patentability for PCT/US2009/069395, filed Dec. 23, 2009, mailed Aug. 9, 2011, 12 pgs.

Plavnik, Zinovy; International Search Report and Written Opinion for PCT/US2009/069395, filed Dec. 23, 2009, mailed Mar. 23, 2010, 13 pgs.

Plavnik, Zinovy; Canadian Office Action for serial No. 2,748,263, filed Dec. 23, 2009, mailed Apr. 16, 2013, 4 pgs.

Plavnik, Zinovy; International Search Report and Written Opinion for PCT Application No. PCT/US15/34440, filed Jun. 5, 2015, mailed Sep. 14, 2015, 9 pgs.

Plavnik, Zinovy; PCT Application entitled: Indirect Acoustic Drying System and Method having serial No. PCT/US15/34440, filed Jun. 5, 2015, 38 pgs.

Plavnik, Zinovy; PCT Application entitled: Acoustic-Assisted Heat and Mass Transfer Device having serial No. PCT/US15/42028, field Jul. 24, 2015, 71 pgs.

Plavnik, Zinovy; U.S. Provisional Patent Application entitled: Acoustic-Assisted Heat and Mass Transfer Device, U.S. Appl. No. 62/028,656, filed Jul. 24, 2014; 21 pgs.

Wikipedia; Article entitled "Mersenne's Law", located at http://en.wikipedia.org/wiki/Mersenne%27s_Laws, accessed on May 2, 2014, 2 pgs.

Incropera, et al.; "The Effects of Turbulence", Fundamentals of Heat and Mass Transfer, 1996, 7 pgs.

Kelva; Web Cleaner—Web cleaner head BR41/Filter and fan unit K-22; internet article—www.kelva.com; document available prior to Feb. 9, 2008; Lund, Sweden; 4 pgs.

(56) References Cited

OTHER PUBLICATIONS

Kohler, Herbert B.; "Modern Rod Coaters", available at www.kohlercoating.com/reference/refpdfs/HBKrodcoater.PDF, publicly available prior to Feb. 9, 2008, 7 pgs.
Morin, David; "Chapter 7—2D Waves and other topics", available at http://www.people.fas.harvard.edu/~djmorin/book.html, publicly available prior to Jul. 1, 2013, 11 pgs.
Web Systems Inc.; Ultra Web Cleaner' internet article—www.wsinfo.com/index.html; Printed Dec. 7, 2008; 6 pgs.
Wikipedia; Article entitled "Coating", located at http://en.wikipedia.org/wiki/Coating, accessed on Apr. 25, 2014, 5 pgs.
Plavnik, Zinovy Zalman; Non-Final Office Action for U.S. Appl. No. 14/321,354, filed Jul. 1, 2014, mailed Nov. 16, 2016, 48 pgs.
Plavnik, Zinovy; Extended European Search Report for serial No. 09839835.7, filed Dec. 23, 2009, mailed Oct. 26, 2016, 14 pgs.
Plavnik, Zinovy; Applicant Initiated Interview Summary for U.S. Appl. No. 14/321,354, filed Jul. 1, 2014, mailed Dec. 28, 2016, 3 pgs.
Plavnik, Zinovy; International Preliminary Report on Patentability for PCT Application No. PCT/US15/34440, filed Jun. 5, 2015, mailed Jan. 12, 2017, 8 pgs.
Plavnik, Zinovy; International Preliminary Report on Patentability for Serial No. PCT/US15/42028, filed Jul. 24, 2015, mailed Feb. 2, 2017, 7 pgs.

* cited by examiner

ACOUSTIC-ASSISTED HEAT AND MASS TRANSFER DEVICE

REFERENCE TO RELATED APPLICATIONS

This application claims the benefit of U.S. Provisional Application No. 62/028,656, filed Jul. 24, 2014, which is hereby specifically incorporated by reference herein in its entirety.

TECHNICAL FIELD

This disclosure relates to the field of heat and mass transfer. More particularly, this disclosure relates to drying, heating, cooling, curing, sintering, and cleaning with the assistance of acoustics.

BACKGROUND

It has been observed that the majority of energy intensive processes are driven by the rates of the heat and mass transfer. Specific details of a particular application, such as the chemistry involved in drying a material, the temperature and specific properties of the material, the ambient conditions, the resulting water or solvent evaporation rates, and other factors affect the outcome of any drying and/or heating process. These factors also often dictate the speed of the process, which is sometimes critical, and the nature and size of the drying equipment.

The properties of the boundary layer formed next to the surface along which a fluid moves dictate the heat transfer rate at the surface and therefore the drying rate at the surface. Because of the effect of the boundary layer on the heat transfer rate, it can be argued—as Incropera/DeWitt do in their textbook "Fundamentals of Heat and Mass Transfer"—that heat transfer rates are higher for turbulent flow at a surface than for laminar flow at that surface. In modern heat and mass transfer practice, there are several methods to disrupt the boundary layer in order to produce more turbulent flow and therefore more heat transfer One method of disrupting the boundary layer, in order to increase the heat transfer rate or for any other purpose, and therefore the drying rate of a wet surface, is to focus acoustic sound waves or oscillations such as ultrasonic waves or oscillations—and also heated air in various embodiments—at the surface of the material or coating being dried as shown in U.S. Patent Publication No. 2010-0199510 to Plavnik, published Dec. 12, 2010, which issued as U.S. Pat. No. 9,068,775 on Jun. 30, 2015, both of which are hereby incorporated by reference in their entireties. This aforementioned publication disclosed one method of drying with the assistance of an intense high frequency linear acoustic field.

SUMMARY

Disclosed is an acoustic energy-transfer apparatus including: an acoustic chest, the acoustic chest defining an inner chamber sized to receive a material to be processed; and an acoustic device positioned within the acoustic chest and oriented to direct acoustic energy towards the material to be processed.

Also disclosed is a method for drying a material, the method including: positioning a material in an acoustic chest including an acoustic device; and directing acoustically energized air from the acoustic device at the material within the acoustic chest.

Disclosed are various systems and methods related to drying, heating, cooling, and cleaning with the assistance of acoustics. Various implementations described in the present disclosure may include additional systems, methods, features, and advantages, which may not necessarily be expressly disclosed herein but will be apparent to one of ordinary skill in the art upon examination of the following detailed description and accompanying drawings. It is intended that all such systems, methods, features, and advantages be included within the present disclosure and protected by the accompanying claims.

BRIEF DESCRIPTION OF THE DRAWINGS

The features and components of the following figures are illustrated to emphasize the general principles of the present disclosure. Corresponding features and components throughout the figures may be designated by matching reference characters for the sake of consistency and clarity.

DETAILED DESCRIPTION

Figures 1A, 1B:
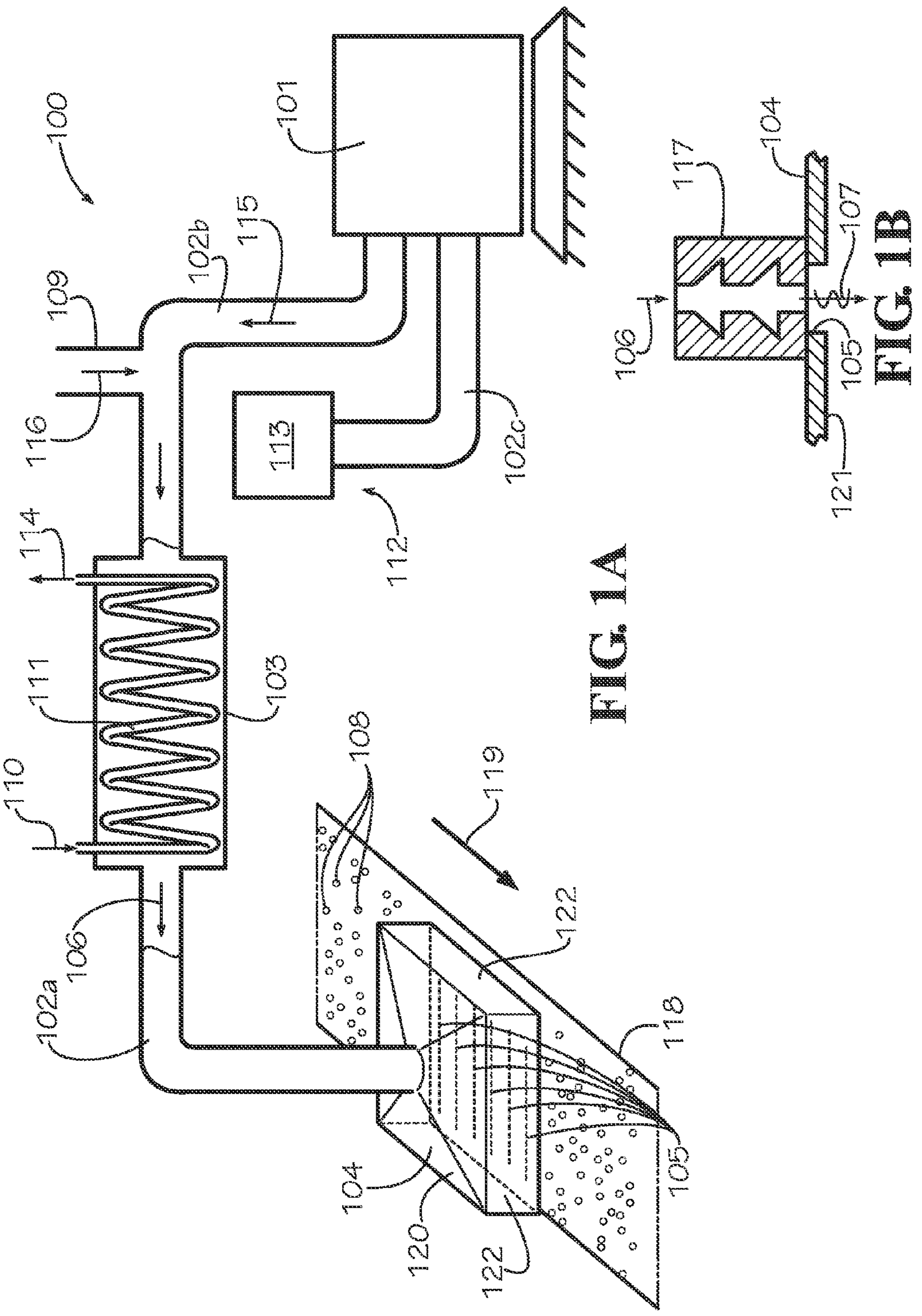
FIG. 1A is a perspective schematic view of an acoustic energy-transfer system in accordance with one embodiment of the current disclosure.
FIG. 1B is a sectional view of an acoustic device of the system of FIG. 1A.

Disclosed are systems that can heat, cool and dry and associated methods, systems, devices, and various apparatus. In various embodiments, these systems include an acoustic dryer. It would be understood by one of skill in the art that the disclosed systems and methods described in but a few exemplary embodiments among many. No particular terminology or description should be considered limiting on the disclosure or the scope of any claims issuing therefrom.

Specifically disclosed are acoustic energy-transfer systems that can dry, heat, cool (including rapidly chill), heat and dry, cool and dry, cure, clean, mix, or otherwise process both continuous and discontinuous materials. An acoustic energy-transfer system that can process a material by drying, curing, cleaning, heating, cooling (including rapidly chilling), sintering, heating and drying, or cooling and drying the material should not be limiting on the current disclosure, however, as additional variations of these processes and combinations of these processes may be used in various embodiments to process the material. Continuous materials include, but are not limited to, such materials as films, coatings, and sheets. Discontinuous materials include, but are not limited to, food and non-food products such as vegetables, meats, fruits, powders, pellets, and granules. The disclosed systems are adaptable to a wide range of processes also including, but not limited to, chilling, flash freezing, freeze-drying, and other drying. In various embodiments, curing a material such as a food material includes preserving the material by drying, smoking, or salting the material.

An energy-transfer apparatus or system such as any one of the acoustic energy-transfer apparatuses or systems disclosed herein need not result in a processed material gaining or losing heat overall for heat-transfer to occur at some level in the process. In various embodiments, energy added in one step of a process may be removed in another process or the energy added to the material may be in a different form than the energy removed from the material—with various energy forms including, but not limited to, acoustic or sound energy, thermal energy, kinetic energy, chemical energy, and electrical energy). An energy-transfer system simply involves the transfer of energy at some point during the overall process, and an acoustic energy-transfer system simply includes the use of acoustic energy to facilitate the process. An apparatus can be any portion of such a system.

Acoustic fields may be used to dry, cool, heat, or even vibrate various materials so as to loosen, mix, or clean the materials. While it is known that acoustic fields can increase thermal transfer, it has been found, surprisingly, that when an object is subjected to chilled acoustic air at the appropriate frequency and intensity, not only is the surface of the object cooled, but rapid cooling is effected throughout the volume of the object. The cooling observed in the bulk of the object appears to be more rapid than would be expected by conventional methods of transferring heat from the object. In various embodiments, an acoustic energy-transfer apparatus or a portion thereof described herein as a dryer is not limited to simply drying the material but may be used to process the material in one or more of the other ways described herein.

In various embodiments, acoustically energized air is air in which acoustic oscillations have been induced. Like sound waves generally, acoustically energized air, in various embodiments, defines an oscillating pressure pattern in which the pressure varies over time and distance. Non-acoustically-energized air will typically have no oscillating pressure pattern but rather will define a constant pressure that may increase or decrease over time and distance but will not oscillate. In various embodiments, an acoustic device defines an acoustic slot from which the acoustically energized air is discharged or directed towards a material to be processed. In various embodiments, acoustically energized material is a material in which acoustic oscillations or vibrations have been induced by acoustically energized air. In various embodiments, acoustically energized material is a material in a fluid such as air or water, the boundary layer of which adjacent the material is disrupted as a result of acoustically energized air.

In various embodiments, an acoustic device is an ultrasonic transducer. In various embodiments, an ultrasonic transducer may be a pneumatic type or an electric type. In various embodiments, a ultrasonic transducer produces acoustic oscillations in a range beyond human hearing. In various embodiments, an acoustic device may generates acoustic energy at sound levels that are below the ultrasonic range (i.e., sound levels that are typically audible to a human). In various embodiments, the range of acoustic waves audible to a human is between approximately 20 Hz and 20,000 Hz, although there is variation between individuals based on their physiological makeup including age and health.

In various embodiments, a system such as any one of the acoustic energy-transfer systems disclosed herein is able to cause axial movement of a material relative to an axial position of the acoustic chest or an acoustic device of the acoustic chest, wherein the acoustic device or acoustic chest may itself be stationary or may be in movement. In various embodiments, a system such as any one of the acoustic energy-transfer systems disclosed herein is able to cause axial movement of an acoustic device relative to an axial position of the material, wherein the material may itself be stationary or may be in movement. In other embodiments, it is not required that the material move relative to an acoustic chest or relative any portion of the system while being processed in order for the material to be dried or processed in any of the other ways disclosed herein. Likewise in various embodiments, it is not required that the acoustic chest or any other portion of the system move relative to the material while being processed in order for the material to be dried or processed in any of the other ways disclosed herein.

In various embodiments, a system such as any one of the acoustic energy-transfer systems disclosed herein is able to cause rotational movement of an acoustic chest or an acoustic device of the acoustic chest relative to a rotational position of the material being processed, wherein the material may itself be stationary or may be in rotational movement. In various embodiments, a system such as any one of the acoustic energy-transfer systems disclosed herein is able to cause axial movement of the material relative to a rotational position of the acoustic device, wherein the acoustic chest or the acoustic device of the acoustic chest may itself be stationary or may be in rotational movement. In other embodiments, it is not required that either the material rotate relative to the acoustic chest or the acoustic device of the acoustic chest while being processed in order for the material to be dried or processed in any of the other ways disclosed herein. Likewise in various embodiments, it is not required that the acoustic chest or any other portion of the system rotate relative to the material while being processed in order for the material to be dried or processed in any of the other ways disclosed herein.

Description of FIGS. 1A and 1B and Related Embodiments

Acoustic energy-transfer system, including for drying and chilling.

The system disclosed in U.S. Pat. No. 9,068,775 to Plavnik may be modified by inserting a heat exchanger between the blower and the acoustic head. This system may also be modified by feeding chilled air into the blower air intake or by inserting a cooling section on the positive pressure line instead of a heater. One embodiment of such a new acoustic energy-transfer system 100 is disclosed in FIGS. 1A and 1B.

Disclosed below is a list of the systems, components, or features or components shown in FIGS. 1A and 1B as designated by reference characters.

100 acoustic energy-transfer system
101 blower
102 tubing
103 heat exchanger
104 acoustic chest
105 acoustic slot
106 chilled air
107 acoustically energized air
108 object (to be processed)
109 injection port
110 inlet coolant
111 cooling piping
112 air intake
113 air intake filter
114 return coolant
115 air
116 additive
117 ultrasonic transducer
118 conveyor belt
119 transport direction
120 top
121 bottom
122 side The acoustic energy-transfer system 100 disclosed in FIG. 1A includes a blower 101 connected to an acoustic chest 104 by tubing 102*a*. FIG. 1A shows chilled air 106 being directed through the acoustic chest 104. The disclosure of chilled air 106 should not be considered limiting on the current disclosure, however, as non-chilled air or even heated air could be used in the acoustic energy-transfer system 100 to otherwise process the objects 108. In various embodiments, the acoustic chest 104 defines a plurality of acoustic devices each defining an acoustic slot 105 in a bottom 121 (shown in FIG. 1B) or other downward-facing side of the acoustic chest 104. The acoustic devices acoustically energize the chilled air 106 so that objects 108—which can also be described as a material—are chilled more effectively as they pass through the acoustically energized air 107 than if acoustically energized air 107 were not used. In various embodiments, acoustically energized air 107 is air in which acoustic oscillations have been induced. Like sound waves generally, acoustically energized air, in various embodiments, defines an oscillating pressure pattern in which the pressure varies over time and distance. Non-acoustically-energized air will typically have no oscillating pressure pattern but rather will define a constant pressure that may increase or decrease over time and distance but will not oscillate. In various embodiments, the acoustic device defines the acoustic slot 105 from which the acoustically energized air 107 is discharged. In various embodiments, the objects 108 are made to pass through the acoustically energized air 107 by transporting the objects 108 on a transport mechanism such as a conveyor belt 118 in a transport direction 119. In various embodiments, a heat exchanger 103 is used to cool the air 115 transported from the blower 101 through tubing 102*b*, air that in various embodiments is drawn from the ambient environment through an air intake 112. In various embodiments, an air intake filter 113 is positioned proximate air intake 112 in order to improve the quality of the air entering the acoustic energy-transfer system 100 through the air intake 112 before entering tubing 102*c*. The disclosure of the chilled air 106 and the heat exchanger 103 should not be considered limiting on the current disclosure, however, as in various embodiments the acoustically energized air 107 need not be chilled for heat transfer to take place (e.g., when the air 115 is at any temperature other than the instantaneous temperature of the objects 108 being cooled).

In various embodiments, the acoustic chest 104 is substantially rectangular in shape when viewed facing a top 120 or the bottom 121 of the acoustic chest 104 or when viewed from any of a plurality of sides 122. However, the disclosure of a substantially rectangular shape for the acoustic chest 104 should not be considered limiting on the present disclosure. The heat exchanger 103 can take any one of many different forms and can utilize any one of many different methods of cooling including, but not limited to, air cooling, water cooling, or cooling by a Peltier device. In various embodiments, a cooling medium such as inlet coolant 110 enters the cooling piping 111 of the heat exchanger 103 and exits from the cooling piping 111 of the heat exchanger 103 as return coolant 114. Depending on the method of cooling or processing, a cooling medium through coolant piping 111 can include, but is not limited to, one or more of various liquids or gasses including chilled water, chilled glycol, ammonia and other so-called "natural" refrigerants like propane (R290) with low or no ozone depletion potential (ODP) and low or no global-warming potential (GWP), whether man-made or naturally-occurring, and R-12 or FREON and other chlorofluorocarbon (CFC), hydrochlorofluorocarbon (HCFC), or hydrofluorocarbon (HFC) refrigerants. In various embodiments, the cooling piping 111 is formed from a metal such as steel. The disclosure of steel for the cooling piping 111 should not be considered limiting on the current disclosure, however, as in various embodiments the cooling piping 111 is formed from a material other than steel or is even formed from a non-metallic material. The disclosure of cooling piping 111 should also not be considered limiting on the current disclosure, however, as the cooling piping 111 of the heat exchanger 103 could be used to transfer heat into the air identified in the current embodiment as chilled air 106.

In various embodiments, a plurality of ultrasonic transducers 117 produce acoustic waves through acoustic slots 105. In various embodiments, the ultrasonic transducers include, but are not limited to, those described in aforementioned U.S. Pat. No. 9,068,775 as being part of the HTI Spectra HE™ Ultra drying system. Each ultrasonic transducer 117 is elongated with a constant cross-section over the length of the ultrasonic transducer 117 and mounted in the acoustic slot 105, and each acoustic slot 105 is sized to provide clearance for the acoustically energized air 107 from the corresponding ultrasonic transducer 117. In various other embodiments, the ultrasonic transducers 117 are not elongated or else vary in cross-section over their length, however, and the disclosure of an elongated shape or a constant cross-section for the ultrasonic transducer 117 should not be considered limiting on the present disclosure. In addition, the disclosure of a plurality of ultrasonic transducers 117 should not be considered limiting on the present disclosure as a single ultrasonic transducer 117 may be employed in various embodiments. In various embodiments, the ultrasonic transducer or other acoustic device defines the acoustic slot 105 and thus the ultrasonic transducer and acoustic slot are inseparable.

The acoustic energy-transfer system 100 of FIG. 1 is able to cool both continuous materials, such as sheets, films, webs, hot blown film, food packaging, nonwoven spun webs; and discrete objects, such as fresh fruit, vegetables, cooked meats, potato chips, waffles, pancakes, breads, steamed vegetables, soups; metal objects such as heat-treated bolts, metal rods, stamped metal, sheet metal, extruded and drawn polymer rods; and glass materials such as heat-treated glass, and spun fiberglass batting.

In various embodiments, an additive 116 is delivered through an injection port 109 and mixed with the air 115 driven by the blower 101. In various embodiments, the additive 116 may include smoke from a smoke source (e.g., using smoldering wood such as cedar wood) or a smoke flavoring, or a sugar or other material. In various embodiments, the additive 116 can be used to additionally flavor foods that are being dried and/or cooled. In various embodiments, the injection port 109 is positioned before the heat exchanger 103. In various other embodiments, the injection port 109 is positioned at a point in the acoustic energy-transfer system 100 at or after the heat exchanger 103. The additive 116 can be a fluid material that becomes gaseous (i.e., is vaporized) before injection or upon injection into the acoustic energy-transfer system 100.

If water moisture or water mist is injected through the injection port 109, the acoustically energized air 107 breaks up the water particles, partially vaporizing them and creating a fine spray or mist. Because the specific heat capacity of water is greater than that of air, much greater heat transfer is possible. In addition, the water such as the water particles in the acoustically energized air 107 can be used to control the rate of drying and water content of a product such as the objects 108.

The airflow through the blower 101 and the geometry of the acoustic chest 104 can be adjusted so that an intense acoustic field is generated as the acoustically energized air 107 exits the acoustic slot 105. In various embodiments, the intensity of the acoustic field and the specific characteristics of the acoustic waveform are adjustable. Typically, this acoustic field has an acoustic pressure in the range of 150-190 dBA, where dBA is sometimes referred to as an "A-weighted" decibel or acoustic pressure measurement. It has been found that an acoustic field in this range can conservatively increase the cooling rate of an object by a factor of 4 to 8 when compared to chilled air that is not acoustically energized. In various embodiments, however, the acoustic pressure may be outside this range. In various embodiments, the temperature of the chilled air 106 is in the range of +20° C. to −50° C., depending upon the application and the end goals. In various embodiments, however, the temperature of the chilled air 106 may be outside this range.

An increased cooling rate made possible by the disclosed acoustic energy-transfer system 100 makes it possible to flash freeze materials, such as foods, while maintaining structure and nutritional value. It is also possible to very rapidly cool cooked foods, such as processed meats, ham, cheeses, fish, and seafood. It is expected that ice made in an acoustic field has a much smaller crystal size due to both increased seeding because of the acoustics traveling through the material, as well as the more rapid heat removal. Typically, in coatings that do include a phase change material, domain size becomes smaller and more uniform when acoustic drying or acoustic cooling technology is used.

In some instances, a food material needs to be chilled or frozen in a rapid continuous manner, such as in high-volume frozen food production (e.g., production of foods including, but not limited to, frozen peas, and frozen corn). In this case, it can be desirable to freeze the fruits and vegetables in such a way that they are separated from each other and do not clump into a frozen mass. Separating each vegetable piece not only increases thermal freezing efficiency, but also makes the food more desirable to some consumers.

In various embodiments, the acoustic energy-transfer system 100 includes the acoustic chest 104, and the acoustic chest 104 further defines the acoustic slot 105 that directs the acoustically energized air 107 towards the objects 108 to be dried, cooled, or heated or otherwise processed. In various embodiments, the object 108 is a granular material that is transported on the conveyor belt 118 past the acoustic chest 104. In various embodiments, the heat exchanger 103 causes the air 115 to transform into the chilled air 106 before the air 115 or the chilled air 106 reaches the acoustic chest 104. In various embodiments, the acoustic energy-transfer system 100 includes the injection port 109 for infusing the air 115 with the additive 116 such as smoke or other flavorings. In various embodiments not requiring the chilling of the objects 108, the chilled air 106 is replaced with heated air (not shown) by using a heat exchanger 103 to heat the air 115.

In various embodiments, the acoustic energy-transfer system 100 dries the objects 108 by positioning at least one ultrasonic transducer 117 a spaced distance from the objects 108, the ultrasonic transducer 117 defined in the bottom 121 of the acoustic chest 104; by forcing the chilled air 106 through the at least one ultrasonic transducer 117; by inducing acoustic oscillations or acoustically energized air 107 in the at least one ultrasonic transducer 117; and by directing the acoustically energized air 107 at the objects 108. In various embodiments, the method of drying the objects 108 further includes chilling the objects 108 by causing the air 115 to become the chilled air 106 before the air 115 or the chilled air 106 reaches the acoustic chest 104. In various embodiments, drying the objects 108 includes infusing the air 115 with an additive 116.

Figures 2A, 2B, 3A, 3B:
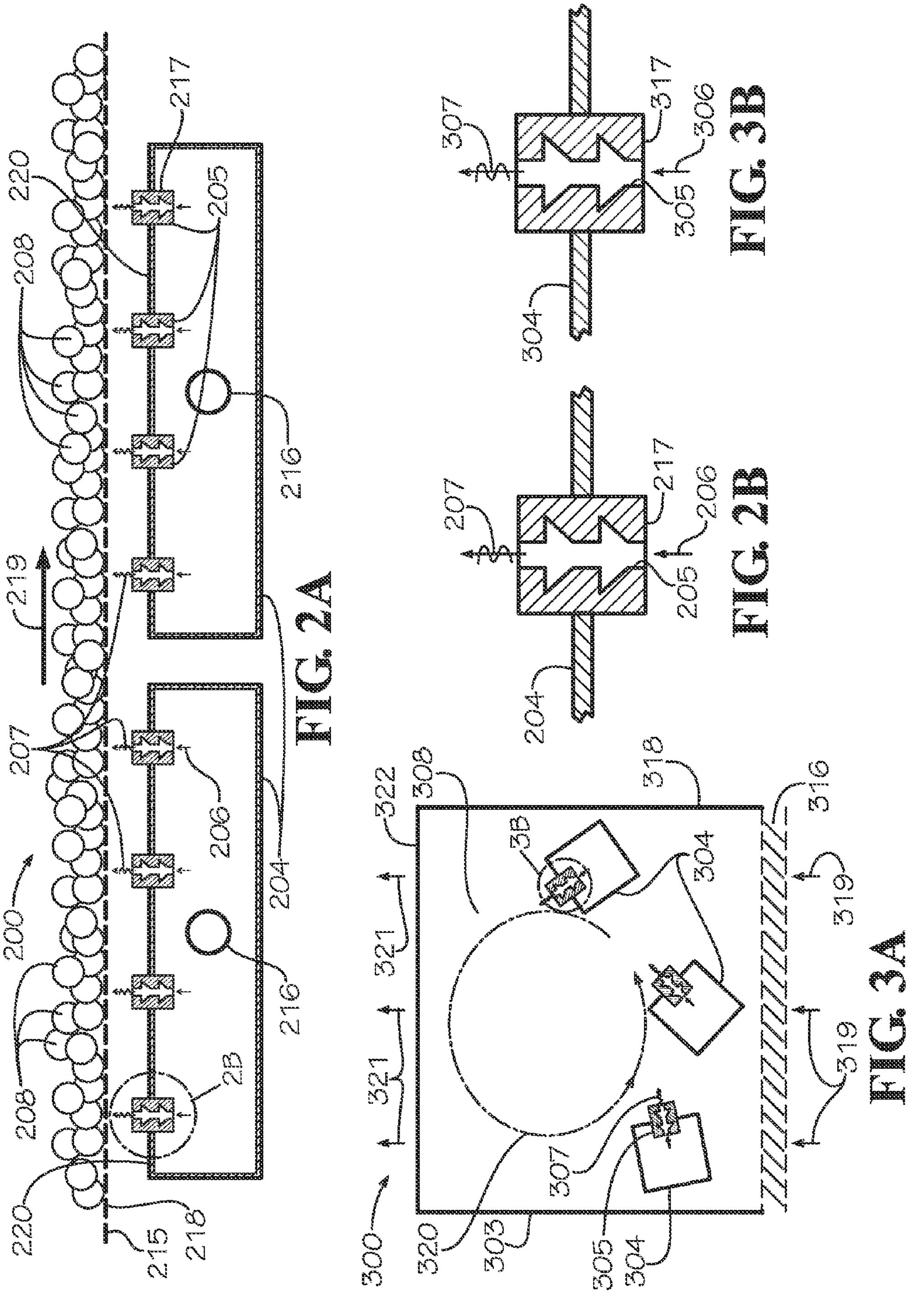
FIG. 2A is a sectional view of a fluidized-bed acoustic energy-transfer system in accordance with one embodiment of the current disclosure.
FIG. 2B is a sectional view of an acoustic device of the system of FIG. 2A taken from detail 2B of FIG. 2A.
FIG. 3A is a sectional view of a batch-wise fluidized-bed acoustic energy-transfer system in accordance with one embodiment of the current disclosure.
FIG. 3B is a sectional view of an acoustic device of the system of FIG. 3A taken from detail 3B of FIG. 3A.

Description of FIGS. 2A and 2B and Related Embodiments

Fluidized bed acoustic energy-transfer system.

One way to separate the materials yet maintain high throughput through an acoustic energy-transfer system is through fluidization. In the fluidization process, discrete objects are levitated against the force of gravity by a controlled air stream directed from beneath a mesh conveyer belt. The amount of air is carefully controlled to effect fluidization, while not blasting the materials with such force that they are ejected from the chilling or drying system. One embodiment of such a new acoustic energy-transfer system 200 is disclosed in FIGS. 2A and 2B.

Disclosed below is a list of the systems, components, or features or components shown in FIGS. 2A and 2B as designated by reference characters.

200 acoustic energy-transfer system
204 acoustic chest
205 acoustic slot
206 inlet air
207 acoustically energized air
208 objects (to be processed)
215 perforated conveyer
216 air inlet
217 ultrasonic transducer
218 transport mechanism
219 transport direction
220 top In various embodiments, inlet air 206 (shown in FIG. 2B) enters an air inlet 216 of an acoustic chest 204 of the acoustic energy-transfer system 200. In various embodiments, the acoustic chest 204 defines a plurality of acoustic slots 205 in a top 220 of the acoustic chest 204, which is upward facing in the current embodiment. Within each of a plurality of acoustic slots 205 as shown in FIG. 2B, an ultrasonic transducer 217 energizes the inlet air 206 so that it becomes acoustically energized air 207. In various embodiments, objects 208—which can also be described as a material—are made to pass through the acoustically energized air 207 by transporting the objects 208 on a transport mechanism 218 such as a perforated conveyor 215 in a transport direction 219. In various embodiments, the objects 208 are chilled or heated as they pass through the acoustically energized air 207 depending on whether the inlet air 206 is chilled or heated.

In various embodiments, each ultrasonic transducer 217 is elongated with a constant cross-section over the length of the ultrasonic transducer and is mounted in or itself defines the acoustic slot 205. In various embodiments, each acoustic slot 205 is sized to provide clearance for the acoustically energized air 207 from the corresponding ultrasonic transducer 217. In various other embodiments, the ultrasonic transducers 217 are not elongated or else vary in cross-section over their length, however, and the disclosure of an elongated shape or a constant cross-section for the ultrasonic transducer 217 should not be considered limiting on the present disclosure. In addition, the disclosure of a plurality of ultrasonic transducers 217 should not be considered limiting on the present disclosure as a single ultrasonic transducer 217 may be employed in various embodiments.

The disclosure of the inlet air 206 being chilled or heated should not be considered limiting on the current disclosure as in various embodiments the acoustically energized air 207 need not be chilled or heated for heat transfer to take place (e.g., when the inlet air 206 is at any temperature other than an instantaneous temperature of the objects 208 being cooled).

A variety of objects 208 can be cooled, heated, or dried using the systems described herein. The disclosed acoustic energy-transfer system 200 can be used for discontinuous food materials including, but not limited to, peas and raspberries. The disclosed acoustic energy-transfer system 200 can also be used for non-food discontinuous materials such as polymer spheres that may be used for the extruding or molding of polymers such as polypropylene (PP), polyethylene (PE), polyvinyl chloride (PVC), polyethylene terephthalate (PET), polyamides such as NYLON, and polylactide (PLA). Use of the disclosed fluidized bed acoustic energy-transfer system 200 with acoustic heat and mass transfer is also useful for the drying of minerals including, but not limited to, gypsum, clays, sands, and limestone.

As the flow of a gas such as the acoustically energized air 207 through a bed of particles such as objects 208 increases, the bed reaches a state where the particles are in "fluid" motion. This occurs when the pressure drop of the gas flowing through the bed equals the gravitational forces of the particles. The onset of this condition is called minimum fluidization.

The Carman-Kozeny equation correlates the various parameters of the particles and the processing parameters with the pressure drop through the bed. It is summarized by equation (1) below.

$$\frac{(-\Delta P)\cdot g}{L} = \frac{(1-\varepsilon)^2\cdot\mu\cdot v\cdot k}{\varepsilon^3\cdot D^2} \tag{1}$$

Where:

ΔP=the pressure drop of the gas through the bed.
g=gravitational constant.
L=the length of the bed.
ϵ=the void volume of the bed.
μ=the viscosity of the gas.
v=the superficial velocity of the gas through the bed.
D=the diameter of the particle spheres.
k=a constant.

A minimum gas velocity, $v_m$, for fluidization to occur can be obtained from equation (1) by writing a force balance around the bed with the length of L and letting this equal the pressure drop through the bed. When this is completed, and certain assumptions are made on the magnitude of terms, equation (2) is generated.

$$v_m = \left(\frac{\varepsilon^3}{1-\varepsilon}\right) \cdot \frac{(\rho_s - \rho) \cdot g \cdot D^2}{150 \cdot \mu} \tag{2}$$

Where:

$\rho$=the density of the gas.

$\rho_s$=the density of the particle spheres.

The $v_m$ term in equation (2) is the minimum gas velocity for the bed to become fluidized and it relates back to the characteristics of the beads and of the fluidizing gas and the void volume of the bed. Beyond the minimum gas velocity, the particles in the bed such as the objects 208 exhibit flow characteristics of ordinary fluids.

The CGS system of units was used in the equation. That is, the units are in centimeters, grams, and seconds. Listed below are the parameters with the appropriate units.

Density ($\rho$) (=) grams/cm$^3$

Gravitational Constant (g) (=) 981 cm/sec$^2$

Particle Diameter (D) (=) cm

Viscosity ($\mu$) (=) grams/cm·sec.

The constant (k) is dimensionless and has a value of 150.

A void volume, $\epsilon$, is the fractional volume of the bed that is completely void. A void volume of 0.45 means that 45 percent of the bed volume is empty and 55 percent is solid. A bed having a void volume of 0.90 is 90 percent empty.

A bed typically initially represents a loose packing of spheres representing the objects 208. The void volume for this type of bed is typically 0.45. To determine the point at which a bed begins to fluidize, this void volume value (0.45) is substituted into equation (2) to calculate the minimum gas velocity for bed fluidization.

However, there is also a maximum gas velocity that this bed can sustain prior to disintegration, when the force of a fluid such as the acoustically energized air 207 causes particles to exit the bed and be carried away by the fluid. This maximum gas velocity is determined by calculating the gas velocity term for a bed that has expanded to a void volume of 0.90. In various embodiments, this value (0.90) represents the onset of the bed being physically "blown" away.

In various embodiments, the acoustic energy-transfer system 200 includes an acoustic chest 204 further defining an acoustic slot 205 capable of producing acoustically energized air 207 having a minimum gas velocity sufficient to maintain a fluidized bed of the objects 208.

In various embodiments, the acoustic energy-transfer system 200 dries the objects 208 by positioning at least one ultrasonic transducer 217 a spaced distance from the objects 208, the ultrasonic transducer 217 included in the acoustic chest 204; by forcing inlet air 206 through the at least one ultrasonic transducer 217; by inducing acoustic oscillations or acoustically energized air 207 in the at least one ultrasonic transducer 217; and by directing the acoustically energized air 207 at the objects 208. In various embodiments, the method of drying or otherwise processing the objects 208 further includes producing acoustically energized air 207 having a minimum gas velocity sufficient to maintain a fluidized bed of the objects 208.

Description of FIGS. 3A and 3B and Related Embodiments

Fluidized-bed batch acoustic energy-transfer system.

Another form of an acoustic energy-transfer device is a batch-wise fluidized bed, capable of drying, cooling, heating, or otherwise treating a batch of material. Any discontinuous material including, but not limited to, polymer beads may be dried, heated, or cooled using such a system. One embodiment of such a new batch-drying acoustic energy-transfer system 300 is disclosed in FIGS. 3A and 3B.

Disclosed below is a list of the systems, components, or features or components shown in FIGS. 3A and 3B as designated by reference characters.

300 acoustic energy-transfer system
303 container
304 acoustic chest
305 acoustic slot
306 inlet air
307 acoustically energized air
308 objects (to be processed)
316 perforated base
317 ultrasonic transducer
318 container wall
319 fluidizing air
320 circulation path (of objects being dried or cooled).
321 exiting air (i.e., air leaving container)
322 top Acoustic air can also be used to convey objects, such as particles of material, fibers, particles of food, dust, and so forth. In this way, the acoustically energized air dries and heats, dries and cools, or otherwise processes the objects by any one of the other processes disclosed herein as the acoustic energy-transfer system 300 conveys the objects.

FIG. 3A discloses one embodiment of this concept including a container 303 having a length measured in a plane that is oblique to the plane containing the geometry shown in FIG. 3A. In various embodiments, the acoustic energy-transfer system 300 includes a plurality of acoustic devices, each defining a circumferential acoustic slot 305. In various embodiments, the container 303 has the shape of a tunnel, where the tunnel extends in a direction that is oblique to the plane containing the geometry shown in FIG. 3A. In various embodiments, the acoustic slots 305 are considered circumferential because they are positioned to direct air towards a circumference of a circulation path 320 of objects 308 being cooled or otherwise processed. The objects 308 can also be described as a material. The acoustic slots 305 may also be considered to be aligned with a tangent line (not shown) of an average circulation path such as the circulation path 320. In various embodiments, some of the objects 308 fall radially inside the circulation path 320 and some of the objects 308 fall radially outside the circulation path 320. In various embodiments, the acoustic slots 305 are defined in the plurality of acoustic chests 304 and are each defined by an ultrasonic transducer 317 (shown in FIG. 3B). In various embodiments, each acoustic slot 305 is defined on the inside of the container 303. In various embodiments, one or more of the plurality of acoustic slots 305 may be directed towards the center of the container 303 or at any other point inside the container 303. In various embodiments, the container 303 is a rectangular tube or a round tube or a container having a different cross-sectional shape.

In various embodiments, inlet air 306 is supplied to each acoustic chest 304 by air inlets (not shown) in each acoustic chest 304. In various embodiments, the inlet air 306 is chilled but the disclosure of chilled air for the inlet air 306 should not be considered limiting on the current disclosure. Within each of a plurality of acoustic slots 305 as shown in FIG. 3B, an ultrasonic transducer 317 energizes the inlet air 306 so that it becomes acoustically energized air 307. In various embodiments, air such as acoustically energized air 307 can be directed axially along and inside the container 303, or at any angle to a plane containing the geometry shown in FIG. 3A, to help propel materials such as the objects 308 down the center of the container 303. In this way, as the acoustically energized air 307 or cooling or drying air acts upon the objects 308 traveling inside the container 303, the objects 308 are also conveyed axially through or down the length of the container 303 by the acoustically energized air 307, at least by the acoustically energized air 307 that is directed axially along the container 303 or by pressure in the container 303 that is able to cause axial movement of the objects 308 relative to an axial position of the acoustic chest 304. In various embodiments, fluidizing air 319 enters the container 303 through a perforated base 316 positioned on and substantially covering or completely covering a bottom of the container 303. In various embodiments, the container 303 defines container walls 318 and the exiting air 321 leaves the container 303 at a plurality of openings (not shown) defined in a top 322 of the container 303.

In various embodiments, the acoustic energy-transfer system 300 includes an acoustic chest 304 further defining a plurality of acoustic slots 305 capable of producing acoustically energized air 307 for batch drying of the objects 308. In various embodiments, fluidizing air 319 causes the objects 308 to become suspended inside the container 303 during the drying process.

In various embodiments, the acoustic energy-transfer system 300 dries the objects 308 by positioning at least one ultrasonic transducer 317 a spaced distance from the objects 308, the ultrasonic transducer 317 included in the acoustic chest 304; by forcing inlet air 306 through the at least one ultrasonic transducer 317; by inducing acoustic oscillations or acoustically energized air 307 in the at least one ultrasonic transducer 317; and by directing the acoustically energized air 307 at the objects 308. In various embodiments, the method of drying the objects 308 further includes producing acoustically energized air 307 having a minimum gas velocity sufficient to suspend the objects 308 inside the container 303.

Description of FIGS. 4A-4D and Related Embodiments

Circumferential tubular acoustic energy-transfer system.

A cylindrically shaped or tubular dryer or "ring chiller" can enable the drying or cooling or other processing of a wide variety of materials. For example, such a dryer can be used for rapid chilling (also known as quenching) of film as it is being blown or for chilling extruded plastic parts or blow-molded objects. It is well known that the quenching rate impacts the microstructure of a polymer, providing different properties when compared to a film that was allowed to cool at a slower rate. The ring chiller can be vertical or horizontal or any angle in between. One embodiment of such an acoustic energy-transfer system 400 is disclosed in FIGS. 4A-4D. Expanding the rings of a ring dryer shown to a much wider diameter than shown enables the drying or cooling of an even wider variety of materials.

Disclosed below is a list of the systems, components, or features or components shown in FIG. 4A and FIG. 4B as designated by reference characters.

Figure 4A:
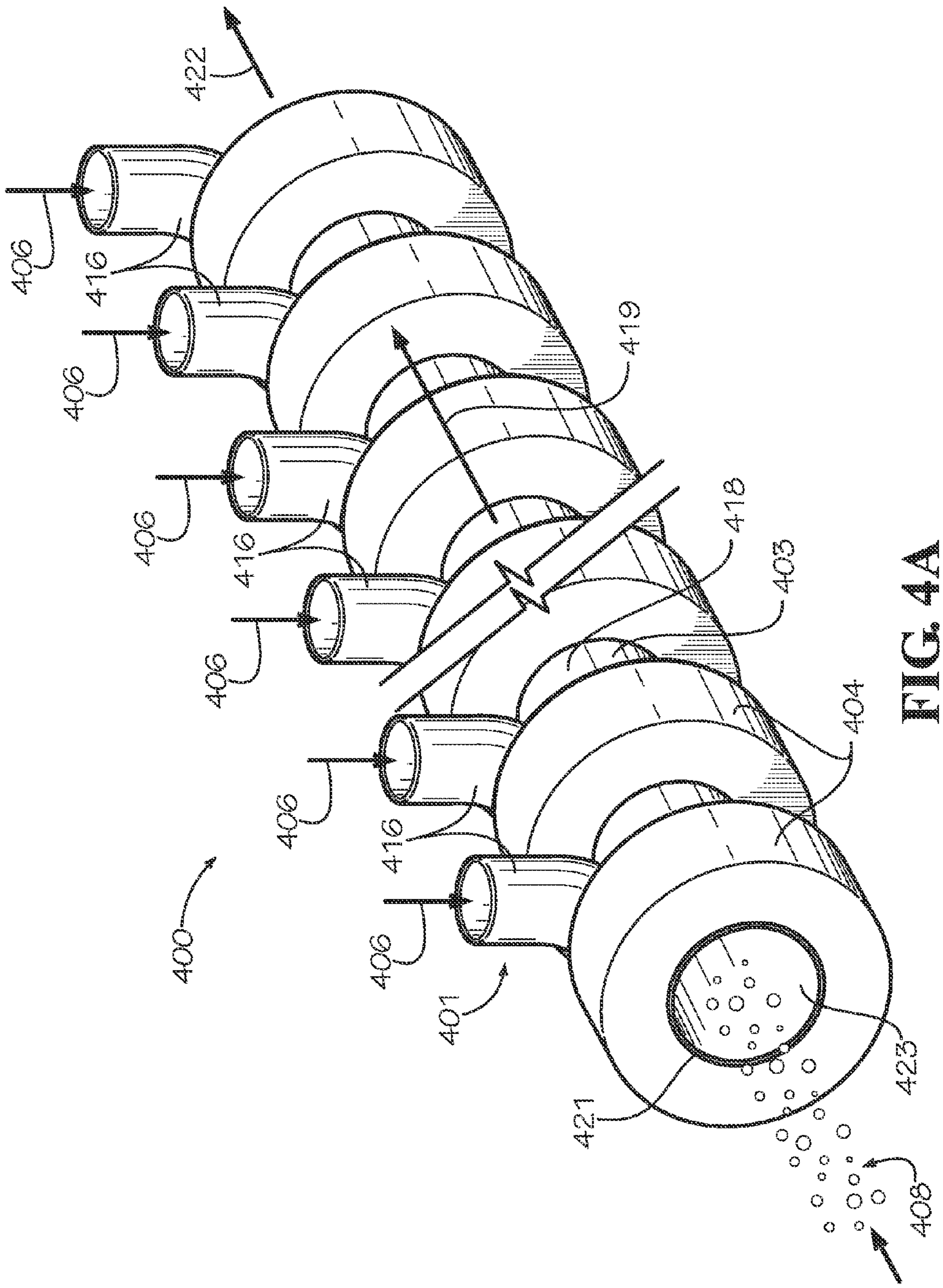
FIG. 4A is a perspective view of a cylindrical acoustic energy-transfer system in which a plurality of ultrasonic nozzles are positioned circumferentially about an object to be dried in accordance with one embodiment of the current disclosure.

400 acoustic energy-transfer system
401 dryer
403 container
404 acoustic chest
405 acoustic slot
406 inlet air
407 acoustically energized air
408 objects (to be processed)
410 central axis
416 air inlet
417 ultrasonic transducer
418 container wall
419 transport direction
421 material inlet
422 material outlet
423 inner chamber FIG. 4A discloses a dryer 401 of the acoustic energy-transfer system 400 as having a plurality of acoustic chests 404 stacked longitudinally (i.e., arranged in series) to form a substantially cylindrically shaped dryer 401 and a container 403. In various embodiments, the dryer 401 may not be exactly cylindrical in shape due to the non-symmetrical design and placement of air inlets 416 and due to the space between adjacent acoustic chests 404. In various embodiments, each of the acoustic chests 404 is an annular ring to which an air inlet 416 is connected. Each acoustic chest 404 defines one or more acoustic slots 405. In various embodiments, an ultrasonic transducer 417 (shown in FIG. 4D) or other acoustic device defines the acoustic slot 405. In various embodiments, the container 403 has the shape of a tunnel, where the tunnel extends along a central axis 410 (shown in FIG. 4D).

In various embodiments, each air inlet 416 is connected to and delivers inlet air 406 through an axial end of an acoustic chest 404 at the top of each acoustic chest 404. The disclosure of an air inlet 416 that is connected to and delivers air through an axial end of an acoustic chest 404 at the top of each acoustic chest 404 should not be considering limiting, however. In various embodiments, one or more air inlets 416 may be connected to a portion of the acoustic chest 404 that is not an axial end of the acoustic chest. In addition, the air inlet 416 may deliver air to multiple portions of the acoustic chest 404 and may do so simultaneously. In various embodiments, a material 408—which can also be described as objects—are transported through an inner chamber 423 defined by a container wall 418 of the container 403. The material 408 may be transported from a material inlet 421 of the container 403 to a material outlet 422 distal the material inlet 421 in a transport direction 419, or the material 408 may be transported in an opposite direction.

Figure 4B:
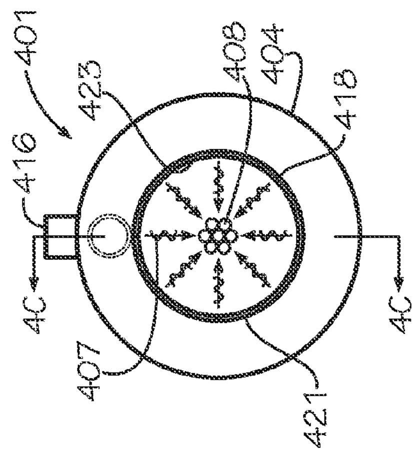
FIG. 4B is an end view of the system of FIG. 4A.

FIG. 4B discloses an end view of the acoustic energy-transfer system 400 showing the material inlet 421, the inner chamber 423, and the air inlet 416. An inner diameter of the inner chamber 423 can be determined based on the objects to be dried and the drying or chilling capacity desired. An outer diameter of the acoustic chest 404 can be determined based on the size of the ultrasonic transducers 417 and the desired amount of inlet air 406. In various embodiments, the inner chamber 423 or the acoustic chest 404 is not circular in cross-section but has a polygonal shape. In each acoustic slot 405 as shown in FIGS. 4B and 4D, an ultrasonic transducer 417 energizes the inlet air 406 so that it becomes acoustically energized air 407. In various embodiments, the material 408 either naturally or by mechanical means (such as a material support like the material support 1028 shown in FIG. 10) is concentrated about a central axis 410 (shown in FIG. 4D) of the dryer 401 as shown in FIG. 4B. In various other embodiments, the material 408 is not concentrated about a central axis 410 but is free to occupy any space inside the inner chamber 423 of the dryer 401.

Figure 4C:
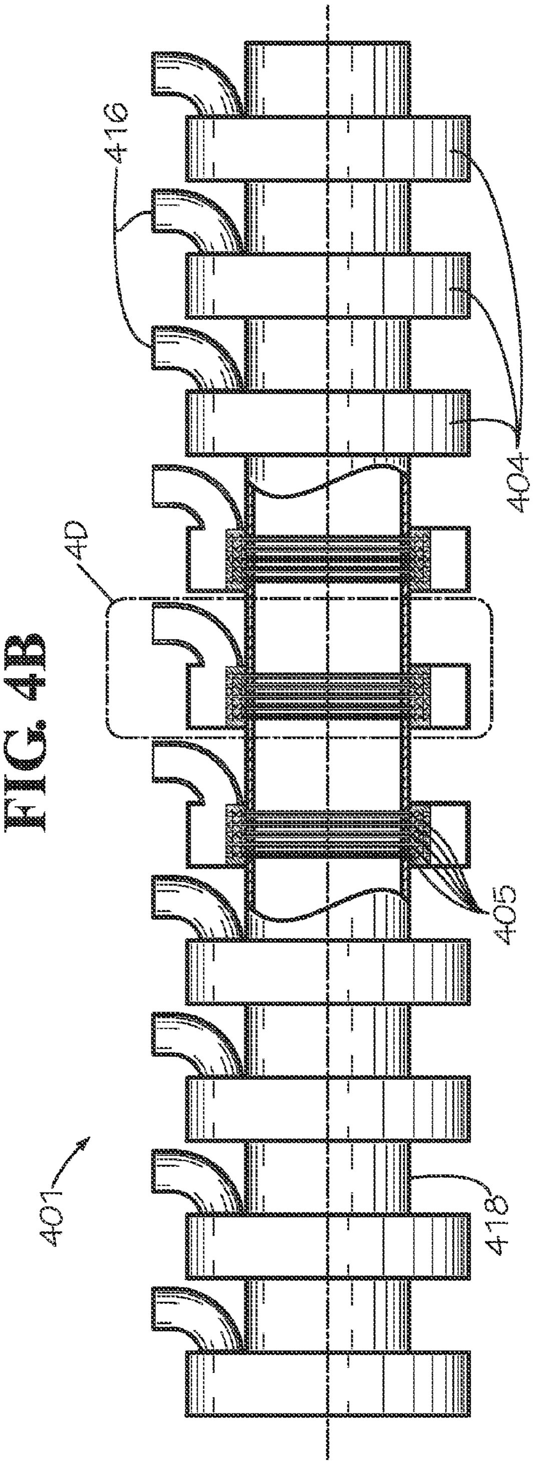
FIG. 4C is a partial cutaway side view of a dryer of the system of FIG. 4A.
Figure 4D:
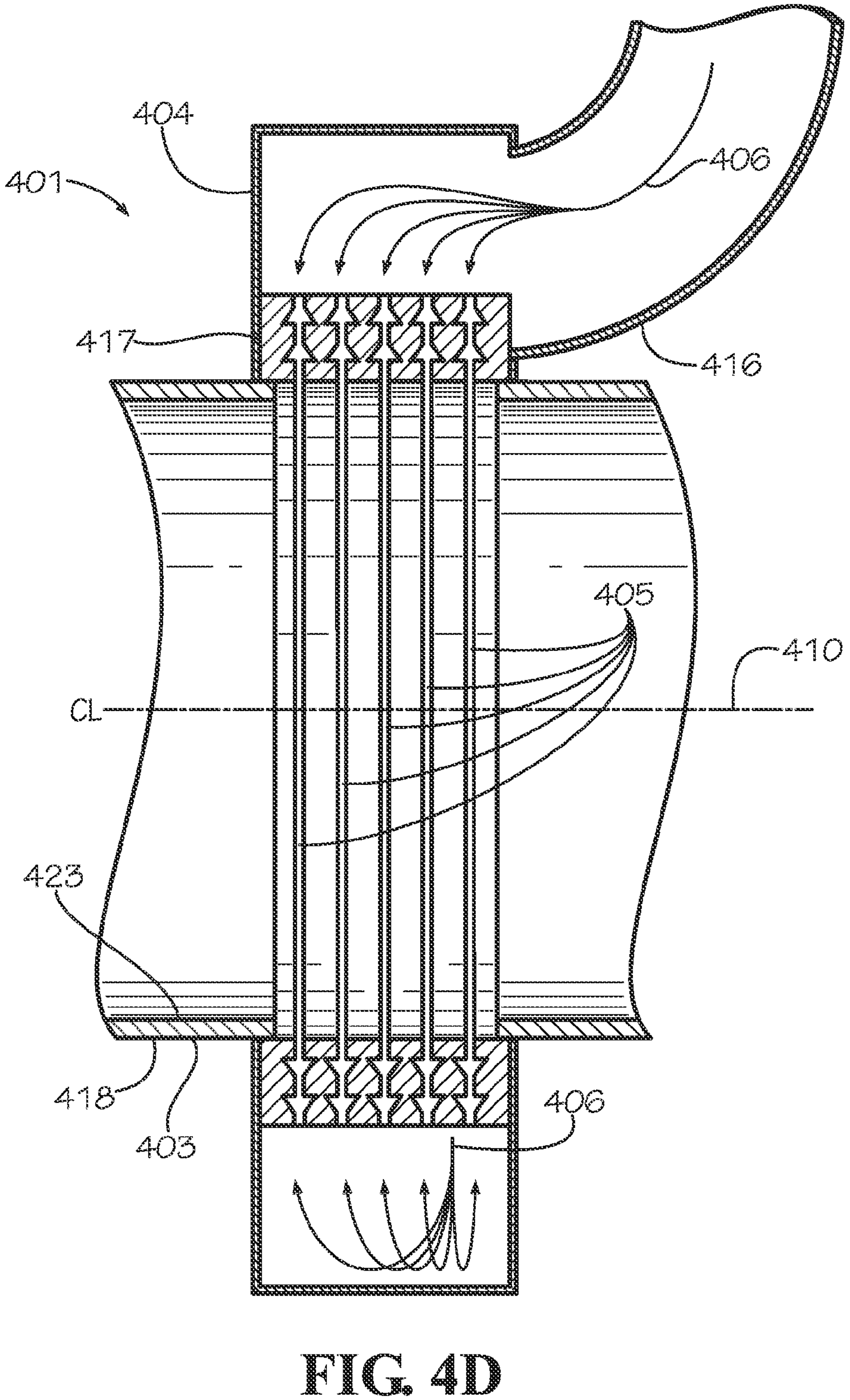
FIG. 4D is a detail cutaway side view of the dryer of FIG. 4C taken from detail 4D of FIG. 4C.

FIGS. 4C and 4D disclose a side view of the dryer 401. FIG. 4C discloses a side view of the entire dryer 401 that also includes a partial cutaway view of the structure of three acoustic chests 404 and air inlets 416. FIG. 4D discloses a partial cutaway view of the structure of a single acoustic chest 404 of the dryer 401. In various embodiments, the ultrasonic transducers 417 define the acoustic slots 405. Each ultrasonic transducer 417 energizes the inlet air 406 to produce acoustically energized air 407 (shown in FIG. 4B) around the circumference of the corresponding acoustic slot 405 and facing an axial center or central axis 410 of the inner chamber 423. As the material 408 passes through the inner chamber 423, the acoustically energized air 407 dries the material 408.

The disclosure of acoustic slots 405 extending around the full circumference of the dryer 401 and the disclosure of multiple acoustic slots 405, however, should not be considered limiting. In various embodiments, the acoustic slots 405 extend a distance less the full circumference of the dryer 401, and in various embodiments a single acoustic slot 405 may be used. In various embodiments, one or more ultrasonic transducers 417 at least partly share a common structure. In various embodiments, each of the ultrasonic transducers 417 is formed into the shape of an annular ring. In various embodiments, the ultrasonic transducers 417 are formed together into a single ultrasonic transducer fitting, an axial end of which can receive a container 403, which in various embodiments includes a separate segment or section between each acoustic chest 404. In various embodiments, the container 403, when broken into separate segments or sections, incorporates a stop feature (not shown) on each end to prevent the container 403 from being inserted into the acoustic chest 404 so far that it blocks an acoustic slot 405. The stop feature may include, but is not limited to, a plurality of dimples around the circumference of the container 403, a mechanically formed flange around the circumference of the container 403, or a rabbeted or stepped outer edge (not shown) around the circumference of the axially outermost ultrasonic transducer or transducers. In various embodiments, the container 403 is a single part and incorporates clearances slots for acoustically energized air 407.

In various embodiments, the acoustic energy-transfer system 400 includes at least one acoustic chest 404 further defining an acoustic slot 405 capable of producing acoustically energized air 407 for drying of the material 408, wherein the material 408 is enclosed within an inner chamber of the acoustic chest 404 and wherein the acoustic slot 405 is defined in a plane oblique to a central axis of the acoustic chest 404 in a cylindrically shaped inner chamber 423 of the acoustic chest 404.

In various embodiments, the acoustic energy-transfer system 400 dries the material 408 by positioning at least one ultrasonic transducer 417 a spaced distance from the material 408, the ultrasonic transducer 417 included in the acoustic chest 404; by forcing the inlet air 406 through the at least one ultrasonic transducer 417; by inducing acoustic oscillations or acoustically energized air 407 in the at least one ultrasonic transducer 417; and by directing the acoustically energized air 407 at the material 408. In various embodiments, the method of drying the material 408 further includes transporting the material 408 through an inner chamber 423 of the dryer 401.

Figure 5:
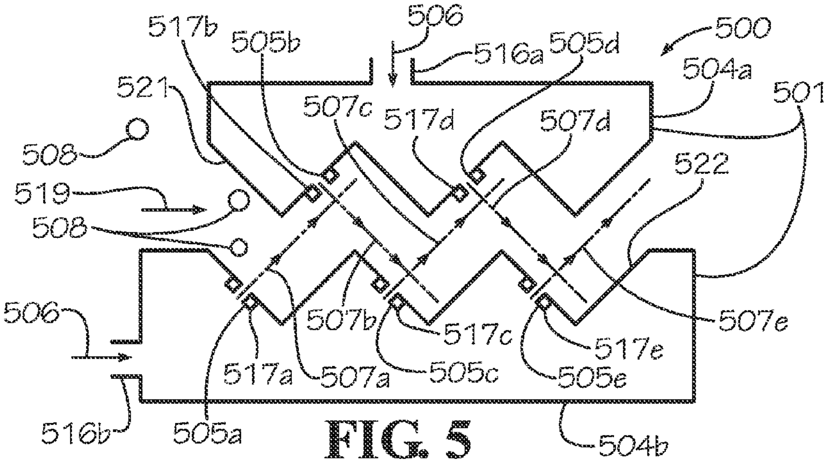
FIG. 5 is a sectional elevation view of a stepped acoustic energy-transfer system in accordance with one embodiment of the current disclosure.

Description of FIG. 5 and Related Embodiments

Stepped acoustic energy-transfer system.

FIG. 5 shows yet another acoustic energy-transfer system for conveying materials as they are being heated or cooled and in various embodiments also dried.

Disclosed below is a list of the systems, components, or features or components shown in FIG. 5 as designated by reference characters.

500 acoustic energy-transfer system
501 dryer
504 acoustic chest
505 acoustic slot
506 inlet air
507 acoustically energized air
508 objects (to be dried or cooled)
516 air inlet
517 ultrasonic transducer
519 transport direction
521 material inlet
522 material outlet FIG. 5 discloses an acoustic energy-transfer system 500 including a dryer 501 and objects 508 to be heated or cooled and in various embodiments dried. The objects 508 can also be described as a material. In various embodiments, the dryer 501 includes an upper acoustic chest 504*a* and a lower acoustic chest 504*b*, each having at least one air inlet 516*a* or air inlet 516*b*, respectively, for receiving inlet air 506. In various embodiments, each of the upper acoustic chest 504*a* and the lower acoustic chest 504*b* is stepped as shown and defines one or more acoustic slots 505 for energizing the inlet air 506. In various embodiments, each acoustic slot 505 is further defined by an ultrasonic transducer 517 that propels acoustically energized air 507 in a direction normal to the surface in which each ultrasonic transducer 517 is assembled. In various embodiments, the ultrasonic transducers 517 are positioned in surfaces facing in the same axial direction as the transport direction 519. In various embodiments, the dryer 501 includes a material inlet 521 and a material outlet 522.

In various embodiments, objects 508 to be heated or cooled and in various embodiments dried are placed in the stream of acoustically energized air 507*a* of the first acoustic slot 505*a*. The acoustically energized air 507*a* either heats or cools and dries or otherwise processes and propels the objects 508 away from the first acoustic slot 505*a*. The first acoustic slot 505*a* directs the objects 508 close to the acoustically energized air 507*b* exiting the second acoustic slot 505*b*, into a zone of high acoustic intensity, where the objects 508 are further heated or cooled and dried. The objects are then propelled further through the dryer 501 and into the path of the acoustically energized air 507*c* exiting the third acoustic jet or acoustic slot 505*c*, close to the exit nozzle of the acoustic slot 505*c*, where the acoustic field is most intense. The acoustically energized air 507*c* exiting the third acoustic nozzle again propels the objects 508 towards the fourth acoustic nozzle jet or acoustic slot 505*d*, while heating or cooling and or drying it, and so on. In various embodiments, the strength or intensity of the acoustic field is constant or decreases as the materials pass by each acoustic jet or acoustic slot 505. In various embodiments, the acoustic energy-transfer system 500 of FIG. 5 is aligned such that the material such as the objects 508 moves consistently in a horizontal or a vertical direction or any other direction between horizontal and vertical relative to a position of the acoustic chest 504, and the alignment of the acoustic energy-transfer system 500 as shown in FIG. 5 should not be considered limiting on the current disclosure.

In various embodiments, an air nozzle (not shown) is positioned on a face of the acoustic chest 504*a*,504*b* that is opposite the face in which one of the ultrasonic transducers 517 is installed. In various embodiments, the air nozzle discharges acoustically energized air (not shown). In various other embodiments, the air nozzle discharges air that is not acoustically energized. In various embodiments, the air nozzles positioned opposite the ultrasonic transducers 517 permit additional adjustment of the velocity of the objects 508 being dried through the acoustic energy-transfer system 500 and permit additional adjustment of the energy transfer achieved during the process.

Materials that can be dried, flash frozen, or heated include foods including, but not limited to, fruits and vegetables and also cereals such as those including, but not limited to, rice, corn, wheat, barley, and soy beans. Other materials that can be processed using the disclosed acoustic energy-transfer system 500 include processed foods including, but not limited to, freeze dried milk, pelletized foods, animal feed, flaked fish; starches including, but not limited to, corn starch, flour, potato starch; and food additives including, but not limited to, xanthan gum. Minerals and inorganic materials can also be dried using the acoustic energy-transfer system 500, such as gypsum, limestone, clays, talk, sodium bicarbonate, and other materials. One advantage of this type of system is the ability to dry materials at low temperature. Sodium bicarbonate, for example, is a thermally unstable material that releases carbon dioxide and water to form sodium carbonate if heated. Drying materials at low temperature can be counterintuitive because heat transfer rate generally decreases at temperature decreases, all other variables being equal. Evaporation using many conventional methods, for example, would require heat in order to supply the energy necessary for the water to change from a liquid phase to a vapor or gas phase.

Organic materials, such as pharmaceutical actives, food supplements, vitamins, and so forth may also be thermally unstable, producing unwanted decomposition products, if heated for too long or at too high temperatures. Such materials may benefit from the ability to be dried rapidly at low temperature, hence avoiding decomposition.

In various embodiments, the acoustic energy-transfer system 500 includes at least one acoustic chest 504 further defining an acoustic slot 505 capable of producing acoustically energized air 507 for drying and in some embodiments also transporting the objects 508. In various embodiments, the at least one acoustic chest 504 includes one or more stepped sections.

In various embodiments, the acoustic energy-transfer system 500 dries the objects 508 by positioning at least one ultrasonic transducer 517 a spaced distance from the objects 508, the ultrasonic transducer 517 included in the acoustic chest 504; by forcing inlet air 506 through the at least one ultrasonic transducer 517; by inducing acoustic oscillations or acoustically energized air 507 in the at least one ultrasonic transducer 517; and by directing the acoustically energized air 507 at the objects 508. In various embodiments, the method of drying the objects 508 further includes producing acoustically energized air 507 having a minimum gas velocity sufficient to propel the objects 508 through the dryer 501.

Figure 6:
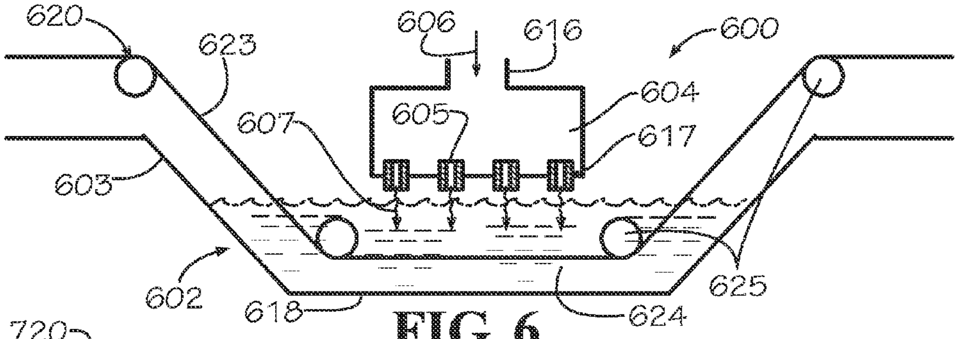
FIG. 6 is a sectional elevation view of an acoustic energy-transfer system in accordance with one embodiment of the current disclosure that utilizes an acoustically charged fluid bath that is energized from above.

Description of FIG. 6 and Related Embodiments

Acoustically charged water bath acoustic energy-transfer system.

Because it is believed that high-intensity acoustic fields increase heat and mass transfer by diminishing or mixing the boundary layer, the acoustic nozzles of the current disclosure can be coupled with cooling water baths to increase the rate of cooling and quenching in water-based cooling processes. Such water-based cooling processes include, but are not limited to, those processes used in polymer extrusion, the drawing of metal rods, and so forth. Such an acoustic energy-transfer system 600 is shown in FIG. 6 as a cooling system.

Similarly, with a reduction in the boundary layer, material exchange from the surface of a material into the bulk liquid phase is accelerated. In this way, an acoustically charged water bath may be used to enhance washing, as well as to accelerate water treatment processes such as the dyeing and finishing of fabrics.

Disclosed below is a list of the systems, components, or features or components shown in FIG. 6 as designated by reference characters.

600 acoustic energy-transfer system
602 water bath
603 container
604 acoustic chest
605 acoustic slot
606 inlet air
607 acoustically energized air
616 air inlet
617 ultrasonic transducer
618 container wall
620 transport mechanism
623 material (to be cooled)
624 coolant liquid
625 idler roller FIG. 6 discloses an acoustic energy-transfer system 600 including an acoustic chest 604, a water bath 602, a transport mechanism 620, and material 623 to be cooled. In various embodiments, the acoustic chest 604 includes an air inlet 616 and defines a plurality of acoustic slots 605. In various embodiments, an ultrasonic transducer 617 of the acoustic chest 604 defines each acoustic slot 605. In various embodiments, the water bath 602 includes a coolant liquid 624 and a container 603, the container 603 including container walls 618 for holding the coolant liquid 624. In various embodiments, the transport mechanism 620 includes idler rollers 625 and a drive mechanism (not shown). In various embodiments, each acoustic slot 605 energizes the inlet air 606 to produce acoustically energized air 607 in a direction normal to the surface of the material 623.

In various embodiments, the acoustic energy-transfer system 600 includes an acoustic chest 604 further defining an acoustic slot 605 capable of producing acoustically energized air 607; a water bath 602 including a coolant liquid 624 for receiving and enclosing the material 608, wherein the acoustically energized air 607 is directed towards the material 608 while the material 608 is submerged inside the coolant liquid 624.

In various embodiments, the acoustic energy-transfer system 600 dries the material 608 by positioning at least one ultrasonic transducer 617 a spaced distance from the material 608, the ultrasonic transducer 617 included in the acoustic chest 604; by forcing inlet air 606 through the at least one ultrasonic transducer 617; by inducing acoustic oscillations or acoustically energized air 607 in the at least one ultrasonic transducer 617; and by directing the acoustically energized air 607 at the material 608. In various embodiments, the method of drying the material 608 further includes directing the acoustically energized air 607 at the material 608 while the material 608 is submerged inside the coolant liquid 624.

Figure 7:
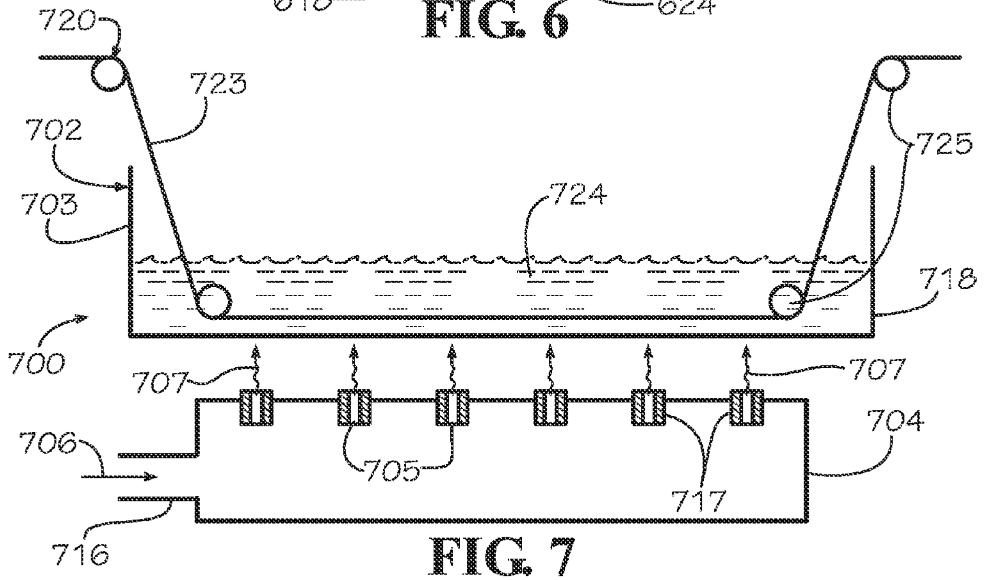
FIG. 7 is a sectional elevation view of an acoustic energy-transfer system in accordance with one embodiment of the current disclosure that utilizes an acoustically energized fluid bath that is energized from below.

Description of FIG. 7 and Related Embodiments

Acoustically charged water bath acoustic energy-transfer system that is energized from beneath.

Instead of directly energizing the cooling fluid, the bath may be energized with acoustic energy by acoustically energized air directly impinging on a water bath container, as shown in FIG. 7.

Disclosed below is a list of the systems, components, or features or components shown in FIG. 7 as designated by reference characters.

700 acoustic energy-transfer system
702 water bath
703 container
704 acoustic chest
705 acoustic slot
706 inlet air
707 acoustically energized air
716 air inlet
717 ultrasonic transducer
718 container wall
720 transport mechanism
723 material (to be cooled)
724 coolant liquid
725 idler rollers FIG. 7 discloses an acoustic energy-transfer system 700 that is a cooling system including an acoustic chest 704, a water bath 702, a transport mechanism 720, and material 723 to be cooled. In various embodiments, the acoustic chest 704 includes an air inlet 716 and defines a plurality of acoustic slots 705. In various embodiments, an ultrasonic transducer 717 of the acoustic chest 704 defines each acoustic slot 705. In various embodiments, the water bath 702 includes a coolant liquid 724 and a container 703, the container 703 including container walls 718 for holding the coolant liquid 724. In various embodiments, the transport mechanism 720 includes idler rollers 725 and a drive mechanism (not shown). In various embodiments, each acoustic slot 705 energizes the inlet air 706 to produce acoustically energized air 707 in a direction normal to the surface of the material 723.

In various embodiments, the acoustic energy-transfer system 700 includes an acoustic chest 704 further defining at least one acoustic slot 705 capable of producing acoustically energized air 707; a water bath 702 including a coolant liquid 724 for receiving and enclosing the material 708, wherein the acoustically energized air 707 is directed towards the material 708 from below the water bath 702 while the material 708 in submerged inside the coolant liquid 724.

In various embodiments, the acoustic energy-transfer system 700 dries the material 708 by positioning at least one ultrasonic transducer 717 a spaced distance from the material 708, the ultrasonic transducer 717 included in the acoustic chest 704; by forcing inlet air 706 through the at least one ultrasonic transducer 717; by inducing acoustic oscillations or acoustically energized air 707 in the at least one ultrasonic transducer 717; and by directing the acoustically energized air 707 at the material 708. In various embodiments, the method of drying the material 708 further includes directing the acoustically energized air 707 at the material 708 from below the water bath 702 while the material 708 is submerged inside the coolant liquid 724.

Figure 8:
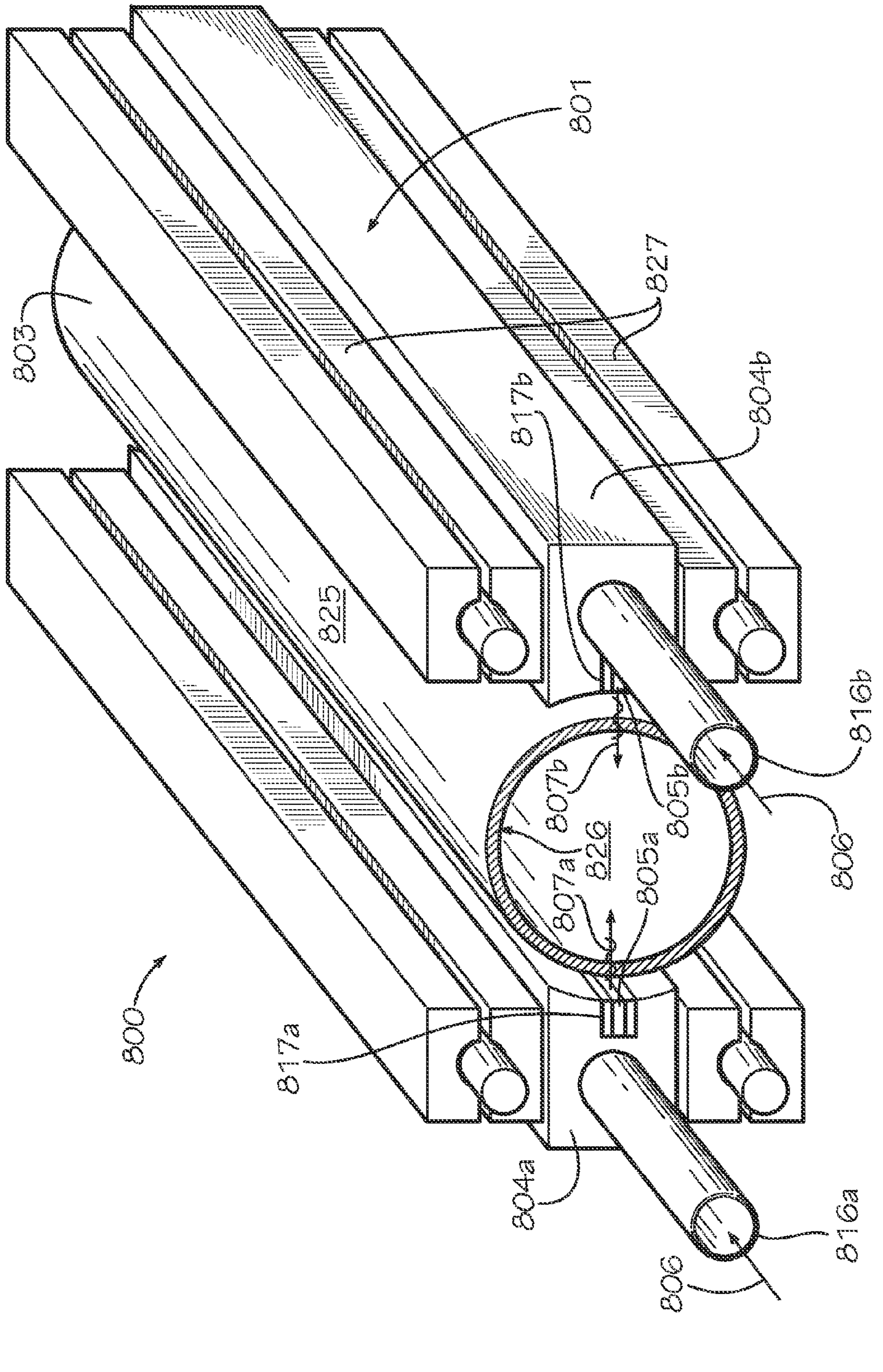
FIG. 8 is a partial cutaway perspective view of an acoustic energy-transfer system for cleaning the inside of a tube without directly accessing the interior of the tube in accordance with one embodiment of the current disclosure.

Description of FIG. 8 and Related Embodiments

Acoustic device for mixing viscous material coating the inside of a tube with a low viscosity cleaner without directly accessing the interior of the tube.

The secondary mixing due to the presence of intense acoustic fields is useful for mixing fluids of very different viscosities and rheologies (alternately, rheometries). For instance, despite being water dispersible, tomato ketchup is difficult to rinse off of plates without some kind of agitation. Properties such as these may prove problematic for cleaning in the food manufacturing industry. Long pipes used to transport thick materials, such as ketchup, mayonnaise, mustard, chocolate, sauces etc., need to be cleaned periodically. FIG. 8 shows an acoustic mixer that can help clean pipes and vessels with interiors that are difficult to access.

Disclosed below is a list of the systems, components, or features or components shown in FIG. 8 as designated by reference characters.

800 acoustic energy-transfer system
801 cleaning device
803 pipe
804 acoustic chest
805 acoustic slot
806 inlet air
807 acoustically energized air
816 air inlet
817 ultrasonic transducer
825 exterior surface (of tube)
826 interior surface (of tube)
827 slider mechanism (to reposition the acoustic chest along the pipe)

FIG. 8 discloses an acoustic energy-transfer system 800 that is a cleaning system including a pipe 803, a cleaning device 801 including a pair of acoustic chests 804*a,b*, and a slider mechanism 827. In various embodiments, the acoustic nozzles or acoustic slots 805*a,b* defined by a pair of ultrasonic transducers 817*a,b*, respectively, produce acoustically energized air 807*a,b*, respectively from the inlet air 806 received through air inlets 816*a,b* and direct the acoustically energized air 807*a,b* towards one or more locations on the exterior surface 825 of the pipe 803. The vibrations produced by the acoustically energized air 807*a,b* are conducted to the soiled interior surface 826 of the pipe 803, where secondary currents effect mixing with a cleaning solution. The acoustic chests 804 of the cleaning device 801 may be manually or automatically repositioned along the pipe 803 through the use of slider mechanisms 827, which in various embodiments may use a smooth rod as a guide to slide the cleaning device 801 along the pipe 803. In various embodiments, a drive mechanism (not shown) can be used to move the cleaning device 801 along the pipe 803.

In various embodiments, the acoustic energy-transfer system 800 includes at least one acoustic chest 804 further defining at least one acoustic slot 805 capable of producing acoustically energized air 807; a slider mechanism 827 for repositioning the acoustic chest 804 along a pipe 803, wherein the acoustically energized air 807 is directed towards the exterior surface 825 of the pipe 803 to clean the interior surface 826 of the pipe 803.

In various embodiments, the acoustic energy-transfer system 800 cleans the pipe 803 by positioning at least one ultrasonic transducer 817 adjacent an exterior surface 825 of the pipe 803, the ultrasonic transducer 817 included in the acoustic chest 804; by forcing inlet air 806 through the at least one ultrasonic transducer 817; by inducing acoustic oscillations or acoustically energized air 807 in the at least one ultrasonic transducer 817; and by directing the acoustically energized air 807 at the exterior surface 825 of the pipe 803. In various embodiments, the method of cleaning the pipe 803 further includes injecting an interior of the pipe 803 with a cleaning solution.

Description of FIGS. 9-23 and Related Embodiments

Radial tubular dryer or chiller.

Figure 9:
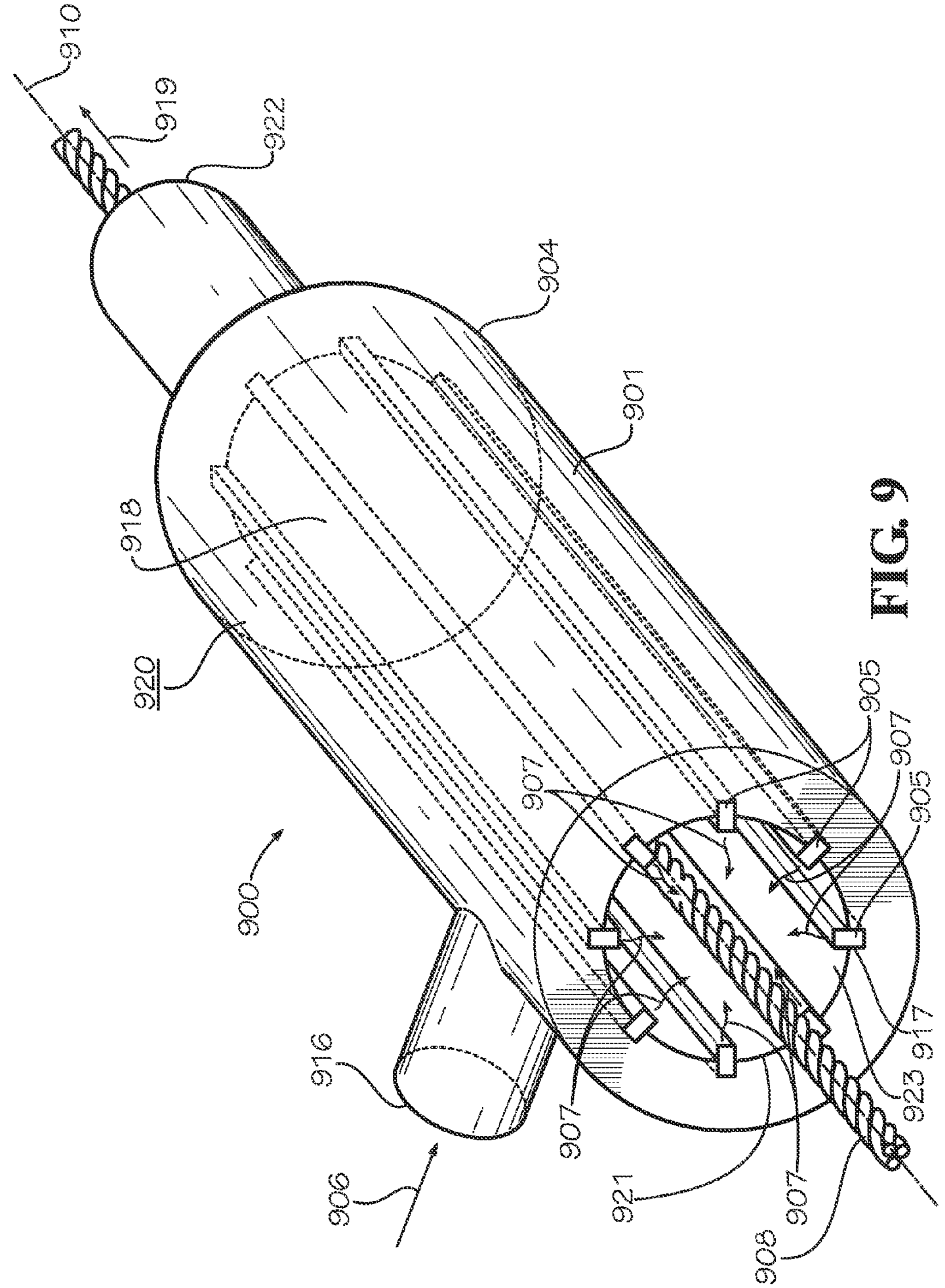
FIG. 9 is a perspective view of a cylindrical acoustic energy-transfer system in accordance with one embodiment of the current disclosure in which a plurality of ultrasonic nozzles are positioned longitudinally about and facing an object to be dried.

In another embodiment, as shown in FIG. 9, the acoustic slots may be defined radially or along an axial direction in an acoustic chest and materials (not shown) may be passed through the middle of the device. Objects or materials such as ropes, yarns, and the like may be dried or chilled using such a device. Objects or materials that are delicate enough not to be able to support their own weight or that are otherwise vulnerable to being damaged during the drying and heating or cooling process may be dried or chilled using such a device. In various embodiments, the material or objects are cylindrical in cross-section and have a diameter that is less than an inner diameter of an inner chamber. However, the disclosure of a material that is cylindrical in cross-section and having a diameter that is less than an inner diameter should not be considered limiting on the current disclosure, however, as the material may be any shape that is able to fit within the acoustic chest and may occupy any portion of the volume of the inner chamber. In addition, the disclosure of a single object or length of object should not be considered limiting on the current disclosure as a plurality of objects or separate lengths of material may be processed simultaneously in various embodiments.

Disclosed below is a list of the systems, components, or features or components shown in FIG. 9 as designated by reference characters.

900 acoustic energy-transfer system
901 dryer
904 acoustic chest
905 acoustic slot
906 inlet air
907 acoustically energized air
908 material (to be dried or cooled)
910 central axis
916 air inlet
917 ultrasonic transducer
918 container wall
919 transport direction
920 outer surface
921 material inlet
922 material outlet
923 inner chamber FIG. 9 discloses an acoustic energy-transfer system 900 including an acoustic chest 904 forming a substantially cylindrically shaped dryer 901 with an inner chamber 923 sized to receive material 908 for drying or cooling. In various embodiments, the acoustic chest 904 has a cylindrical shape. In various embodiments, an air inlet 916 is connected to an outer surface 920 of the acoustic chest 904. In various embodiments, the acoustic chest 904 defines a plurality of acoustic slots 905, and in various embodiments an ultrasonic transducer 917 of the acoustic chest 904 defines each acoustic slot 905. In each of the plurality of acoustic slots 905, an ultrasonic transducer 917 energizes the inlet air 906 so that it becomes acoustically energized air 907. In various embodiments, the material 908 is made to pass through the acoustically energized air 907 by transporting the material 908 using a transport mechanism (not shown) in a transport direction 919. In various embodiments, each ultrasonic transducer 917 is oriented longitudinally along (i.e., in parallel to) a central axis 910 of the dryer 901 in such a way that the path of the acoustically energized air 907 exiting the acoustic slot 905 in a direction normal to a surface of the inner chamber 923 intersects the central axis 910 of the dryer 901 along which the material 908 is positioned.

In various embodiments, the air inlet 916 delivers inlet air 906 to the acoustic chest 904 in the location shown. In various other embodiments, the air inlet 916 may deliver inlet air 906 to multiple portions of the acoustic chest 904 and may do so simultaneously. In various embodiments, the material 908 to be cooled is transported through an inner chamber 923 defined by a chamber wall 918 of the acoustic chest 904. The material 908 may be transported from a material inlet 921 of the dryer 901 to a material outlet 922 distal the material inlet 921 in a transport direction 919, or the material 908 may be transported in an direction opposite the transport direction 919.

Disclosed below is a list of the systems, components, or features or components shown in FIGS. 10-23 as designated by reference characters.

| | |
|---|---|
| 1000 | acoustic energy-transfer system |
| 1001 | dryer |
| 1004 | acoustic chest |
| 1005 | acoustic slot |
| 1006 | inlet air |
| 1007 | acoustically energized air |
| 1008 | material (to be dried) |
| 1010 | central axis |
| 1016 | air inlet |
| 1017 | ultrasonic transducer |
| 1018 | container wall |
| 1019 | transport direction |
| 1021 | material inlet |
| 1022 | material outlet |
| 1023 | inner chamber |
| 1025 | air outlet |
| 1026 | outlet air |
| 1028 | material support |
| 1029 | dryer support |
| 1030 | rotating drive mechanism |
| 1040 | inlet guard |
| 1050 | outlet guard |
| 1060 | seam |
| 1080 | fastener |
| 1090 | fastener |
| 1110 | body |
| 1111 | outer surface |
| 1112 | inner surface |
| 1120 | inlet tube |
| 1130 | end plate |
| 1135 | bore |
| 1140 | end plate |
| 1210 | hub |
| 1211 | outer surface |
| 1212 | inner surface |
| 1220 | collet |
| 1240 | outlet tube |
| 1250 | tab |
| 1280 | fastener |
| 1290 | fastener |
| 1301 | outer surface |
| 1310 | hub |
| 1311 | outer surface |
| 1312 | inner surface |
| 1320 | collet |
| 1330 | cover |

-continued

| | |
|---|---|
| 1340 | outlet tube |
| 1350 | tab |
| 1380 | fastener |
| 1390 | fastener |
| 1401 | outer surface |
| 1402 | inner surface |
| 1405 | hole |
| 1410 | seam |
| 1420 | inner diameter |
| 1421 | inlet |
| 1422 | outlet |
| 1430 | length |
| 1600 | acoustic head |
| 1600' | acoustic head |
| 1690 | attachment hole |
| 1710 | working sprocket |
| 1720 | chain |
| 1730 | wheel |
| 1735 | grip |
| 1740 | drive shaft |
| 1750 | attachment bracket |
| 1752 | adjustment slot |
| 1755 | attachment hole |
| 1760 | fastener |
| 1790 | attachment hole |
| 1810 | end cap |
| 1880 | hole |
| 1905 | end |
| 1910 | cover |
| 1915 | shoulder portion |
| 1920 | bearing portion |
| 1925 | shaft end fitting |
| 1926 | inner surface |
| 1930 | shaft bushing |
| 1931 | axial end surface |
| 1990 | fastener |
| 2005 | rotational direction |
| 2100 | transducer mount |
| 2101 | outer surface |
| 2102 | inner surface |
| 2110 | mount rail |
| 2180 | bore |
| 2190 | fastener |
| 2200 | transducer bar |
| 2202 | working portion |
| 2204 | attachment portion |
| 2210 | upper surface |
| 2220 | lower surface |
| 2230 | inner surface |
| 2240 | outer surface |
| 2250 | first groove |
| 2252 | angled portion |
| 2254 | flat portion |
| 2260 | second groove |
| 2262 | angled portion |
| 2264 | flat portion |
| 2280 | attachment bore |
| 2310 | plate bushing |
| 2311 | inner surface |
| 2320 | outer sleeve |
| 2321 | outer surface |
| 2328 | bore |
| 2380 | bore |
| 2385 | bore |
| 2390 | fastener |
| G1 | gap |
| G2 | gap |

Figure 10:
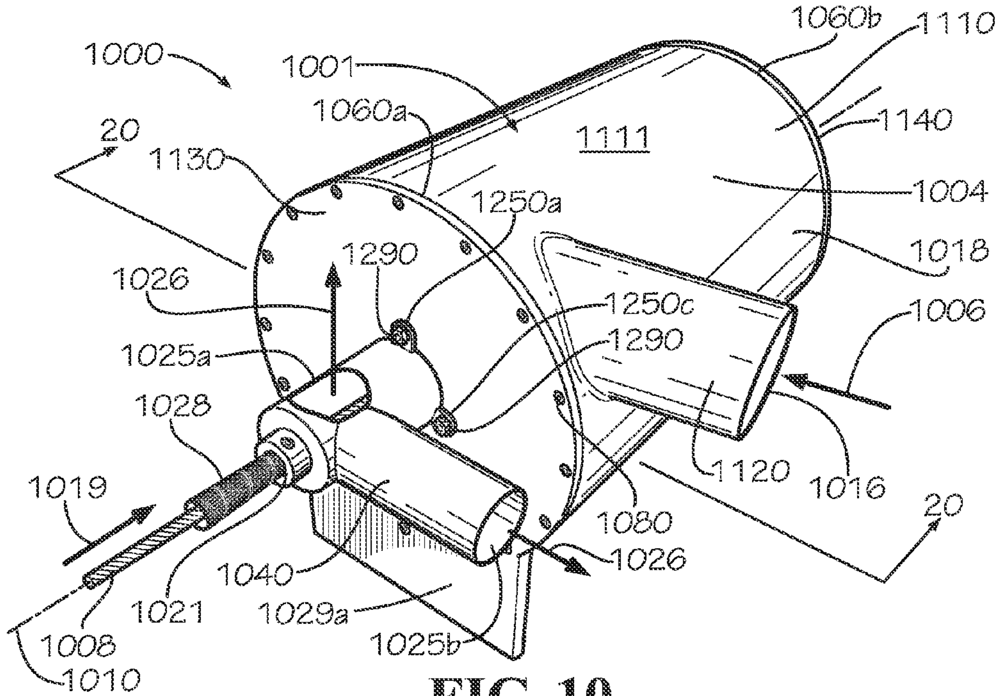
FIG. 10 is a perspective view of an acoustic energy-transfer system taken from an inlet side of the system in accordance with another embodiment of the system.
Figure 11:
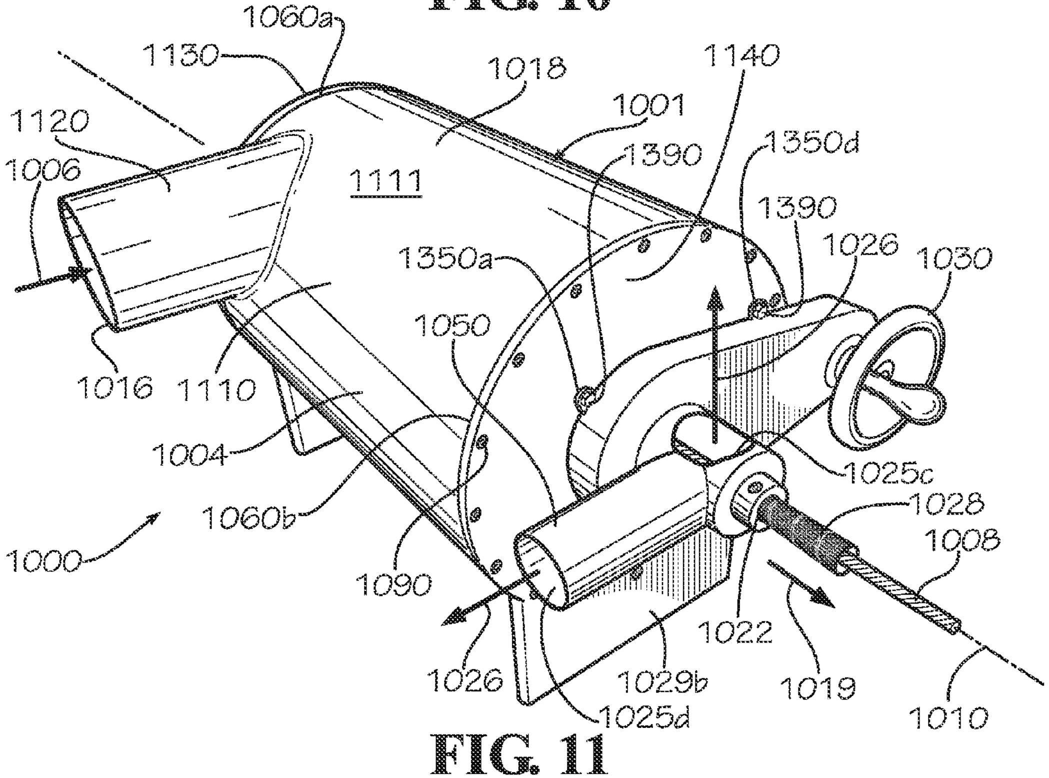
FIG. 11 is a perspective view of the system of FIG. 10 taken from an outlet side of the system.

FIGS. 10 and 11 disclose an acoustic energy-transfer system 1000 for acoustic drying, cooling, or heating of a material (not shown) in accordance with another embodiment of the acoustic energy-transfer system 900 of FIG. 9. In various embodiments, the acoustic energy-transfer system 1000 includes a dryer 1001 and a material 1008 that is to be heated or cooled and dried and a transport mechanism (not shown) to transport the material 1008 through an inner chamber 1023 (shown in FIG. 15) along a material path defined between a material inlet 1021 to a material outlet 1022 from the material inlet 1021 to the material outlet 1022 in a transport direction 1019. In various embodiments, the material path is linear. In various embodiments, the material path includes the entire volume of the inner chamber 1023. In various embodiments, the dryer 1001 includes an acoustic chest 1004 having an air inlet 1016 for receiving inlet air 1006 from the ambient environment or from an air supply system (not shown). In each of a plurality of acoustic slots 1005 (shown in FIG. 18), an ultrasonic transducer 1017 energizes the inlet air 1006 (shown in FIG. 20) so that it becomes acoustically energized air 1007 (shown in FIG. 20). In various embodiments, the acoustic chest 1004 of the dryer 1001 includes a plurality of air outlets 1025*a,b,c,d* for releasing outlet air 1026 to the ambient environment or to an exhaust air collection system (not shown). In various embodiments, the material inlet 1021 or the material outlet 1022 or both the material inlet 1021 and the material outlet 1022 are air outlets. In various embodiments, the dryer 1001 also includes a material support 1028, dryer supports 1029*a, b*, a rotating drive mechanism 1030, an inlet guard 1040, and an outlet guard 1050.

In various embodiments, the acoustic chest 1004 includes a body 1110, an inlet tube 1120, and end plates 1130,1140. In various embodiments, the body 1110, the inlet tube 1120, and the end plates 1130, 1140 define a container wall 1018, an outer surface 1111, an inner surface 1112 (shown in FIG. 18), and an acoustic head 1600 (shown, e.g., in FIG. 16) of the acoustic chest 1004. The end plates 1130,1140 may in various embodiments be assembled to the body 1110 by a plurality of fasteners 1080,1090, respectively, around the perimeter of an axial end of each end plate 1130,1140. In various embodiments, the assembly of the end plates 1130, 1140 to the body 1110 creates seams 1060*a,b*, respectively, which may be filled with a solid or a liquid gasket or sealing material including, but not limited to, a caulk or other adhesive, metal including molten metal filler rod, a paper gasket material, or a polymer gasket material.

The inlet guard 1040 may in various embodiments be assembled to the end plate 1130 by a plurality of fasteners 1290 installed in a plurality of through holes (not shown) of the inlet guard 1040 defined in a plurality of tabs 1250*a,b,c* (1250*b* shown in FIG. 12) of the inlet guard 1040. Likewise, the outlet guard 1050 may in various embodiments be assembled to the end plate 1140 by a plurality of fasteners 1390 installed in a plurality of through holes (not shown) of the outlet guard 1050 defined in a plurality of tabs 1350*a, b,c,d* (1350*b,c* shown in FIG. 13) of the outlet guard 1050.

Figure 12:
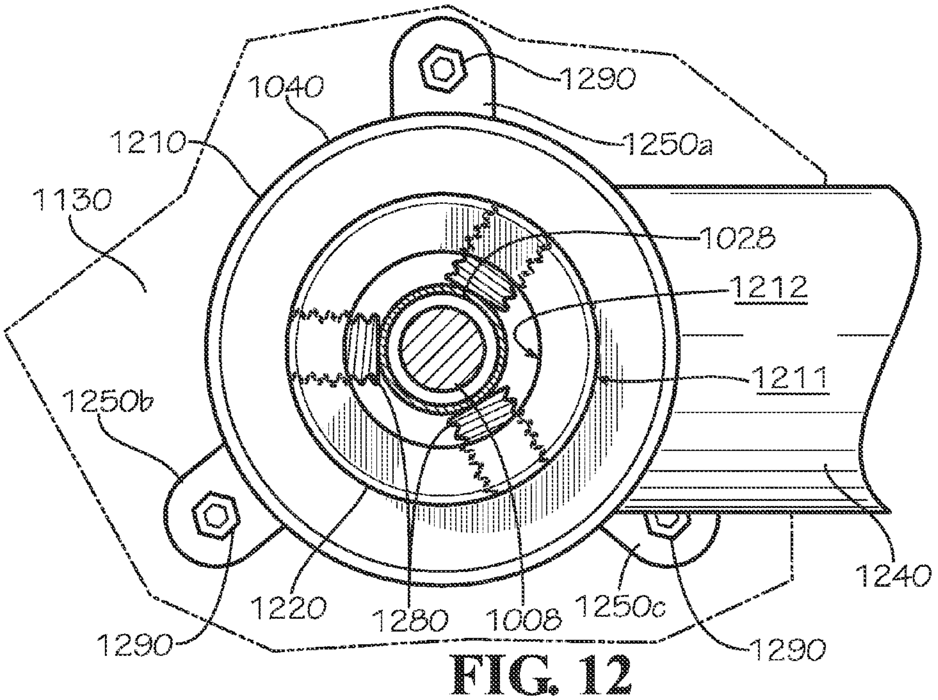
FIG. 12 is a detail end view of a material inlet of the system of FIG. 10.

FIG. 12 discloses a detail view of the material inlet 1021 of the dryer 1001. In various embodiments, the fasteners 1290 assemble the inlet guard 1040 to the end plate 1130. In various embodiments, the inlet guard 1040 includes a hub 1210 and a collet 1220, each concentric with the other and with the material inlet 1021 of the acoustic chest 1004. In various embodiments, the inlet guard 1040 includes the outlet tube 1240. The collet 1220 defines an outer surface 1211 and an inner surface 1212, and in various embodiments a plurality of fasteners 1280—which may be set screws as shown—are assembled between the outer surface 1211 and the inner surface 1212 to hold in position the material support 1028, which in turn supports the material 1008. In various embodiments, the fasteners 1280 may be adjusted with a tool such as an allen wrench to position and grip the material support 1028 as desired.

Figure 13:
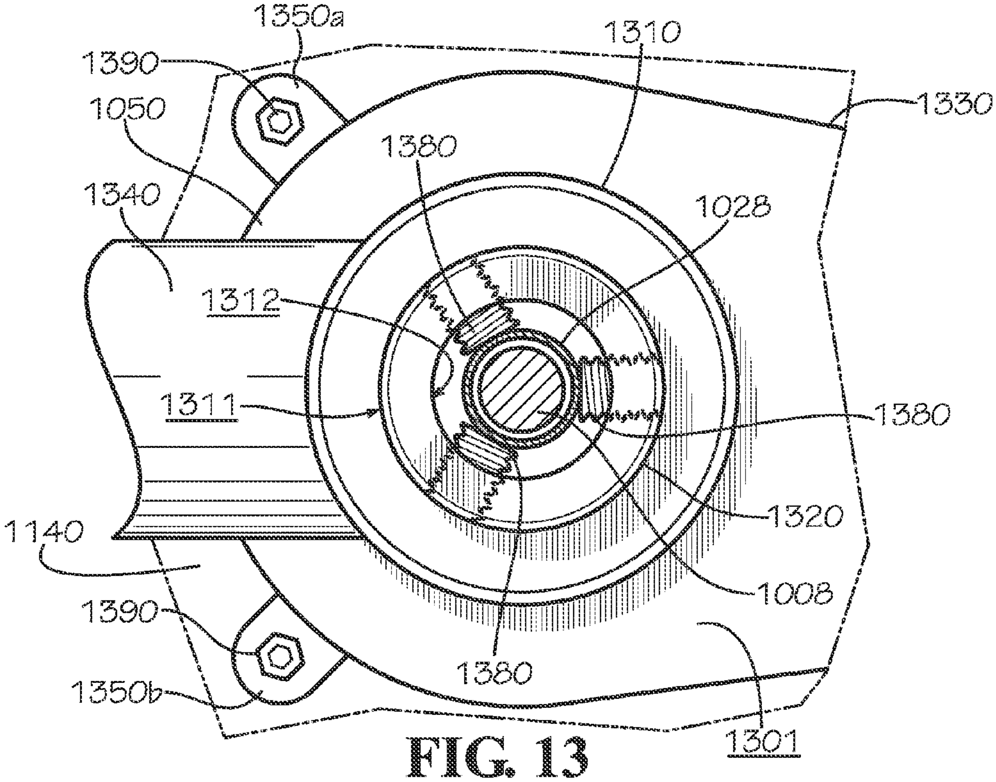
FIG. 13 is a detail end view of a material outlet of the system of FIG. 10.

FIG. 13 discloses a detail view of the material outlet 1022 of the dryer 1001. In various embodiments, the fasteners 1390 assemble the outlet guard 1050 to the end plate 1140. In various embodiments, the outlet guard 1050 includes a hub 1310 and a collet 1320, each concentric with the other and with the material inlet 1021 of the acoustic chest 1004. In various embodiments, the outlet guard 1050 also includes a cover 1330 and an outlet tube 1340 and defines an outer surface 1301. The collet 1320 defines an outer surface 1311 and an inner surface 1312, and in various embodiments a plurality of fasteners 1380—which may be set screws as shown—are assembled between the outer surface 1311 and the inner surface 1312 to hold in position the material support 1028, which in turn supports the material 1008. In various embodiments, the fasteners 1380 may be adjusted with a tool such as an allen wrench to position and grip the material support 1028 as desired.

Figure 14:
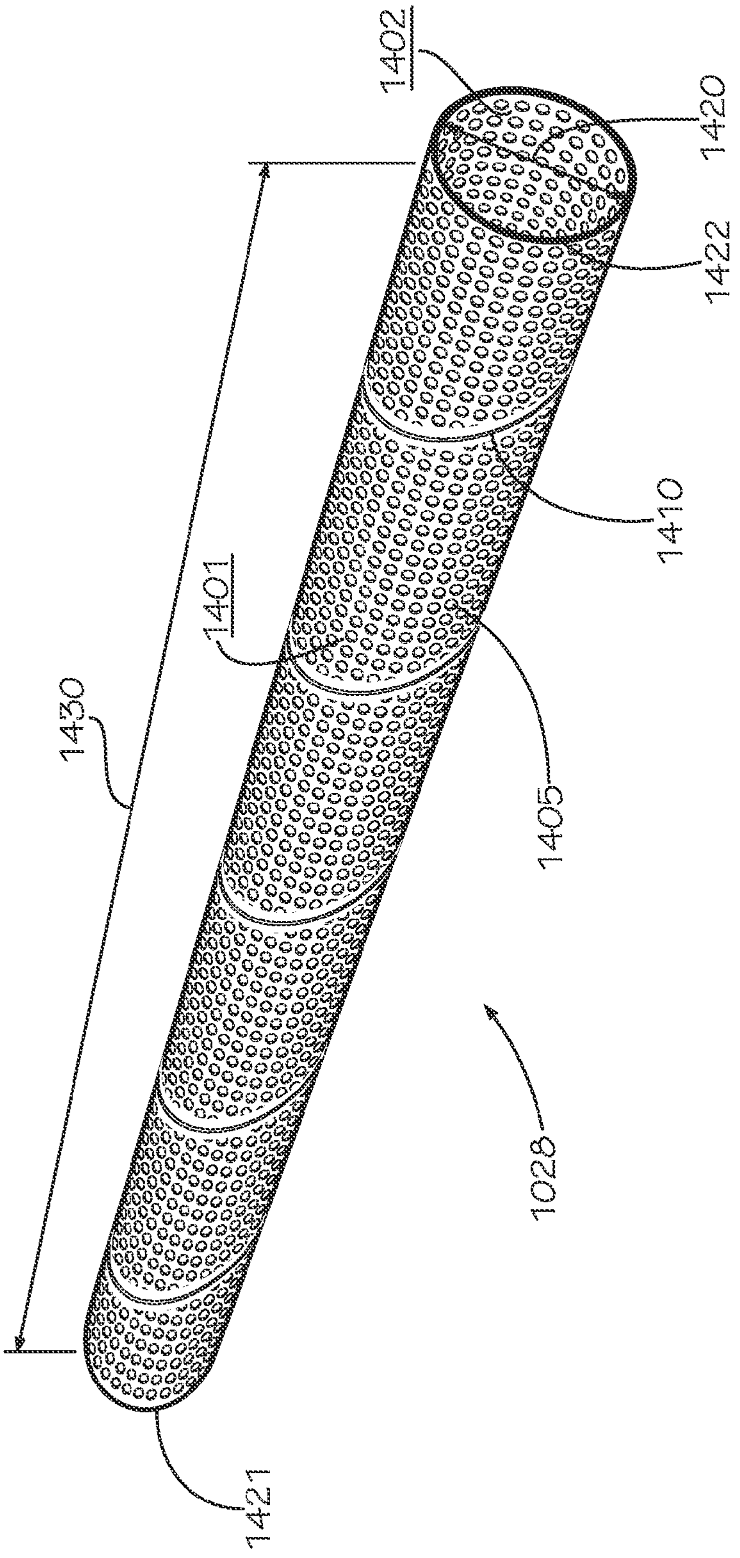
FIG. 14 is a perspective view of a material support of the system of FIG. 10.

FIG. 14 discloses the material support 1028 of the dryer 1001. In various embodiments, the material support 1028 is constant in cross-section and defines an inlet 1421, an outlet 1422, an outer surface 1401, an inner surface 1402, an inner diameter 1420, and a length 1430 sized to receive a variety of materials to be dried and cooled or heated such as the material 1008. In various embodiments, the material support 1028 resembles a pipe or tube as shown and has a cylindrical or other polygonal cross-section. The material support 1028 is a pre-punched spiral-wound and spiral-welded pipe with a seam 1410 in the current embodiment. The material support 1028, however, may be formed or fabricated from any one or more of a variety of methods including, but not limited to, spiral winding and welding from plate, rolling and welding from plate, extruding, casting, and molding. The material support 1028 is fabricated from stainless steel in the current embodiment. The material support 1028, however, may be formed or fabricated from any one or more of a variety of materials including, but not limited to, steel including grades other than stainless steel, other metals, ceramics, polymers, or paper. The material support 1028 defines a plurality of holes 1405, which are circular in the current embodiment and facilitate passage of the acoustically energized air 1007 (shown in FIG. 20) to any material 1008 enclosed within the material support 1028. In various embodiments, an open surface area as a percentage of a total exterior surface area of the material support 1028 is in a range between 30% and 60%. The disclosure of the range of 30-60% should not be considered limiting on the current disclosure, however, as the open surface area may be lower or higher than this range in various embodiments. The disclosure of a plurality of holes 1405, which are circular in shape, should not be considered limiting on the current disclosure, however, as the material support 1028 may define openings that differ in shape from the holes 1405 that are shown. In various embodiments, the material support 1028 is able to not only support the weight of whatever material is enclosed thereby and dried by the dryer 1001, but the material support 1028 is also able to withstand the temperature extremes, the abrasion loads, and other stresses encountered during operation of the dryer 1001. In various embodiments the inlet 1421 or the outlet 1422 or both are cone shaped or fit with rollers to guide the material 1008 into the material support 1028. In various embodiments, the inner surface 1402 or the outer surface 1401 is fabricated in a way that eliminates any burrs or other impediments to the smooth movement of the material 1008 inside the material support 1028 including smooth axial movement relative to the axial position of the material support 1028. In various embodiments, the material support 1028 is fabricated from copper or from a similar material having a relatively high coefficient of thermal conductivity.

Figure 15:
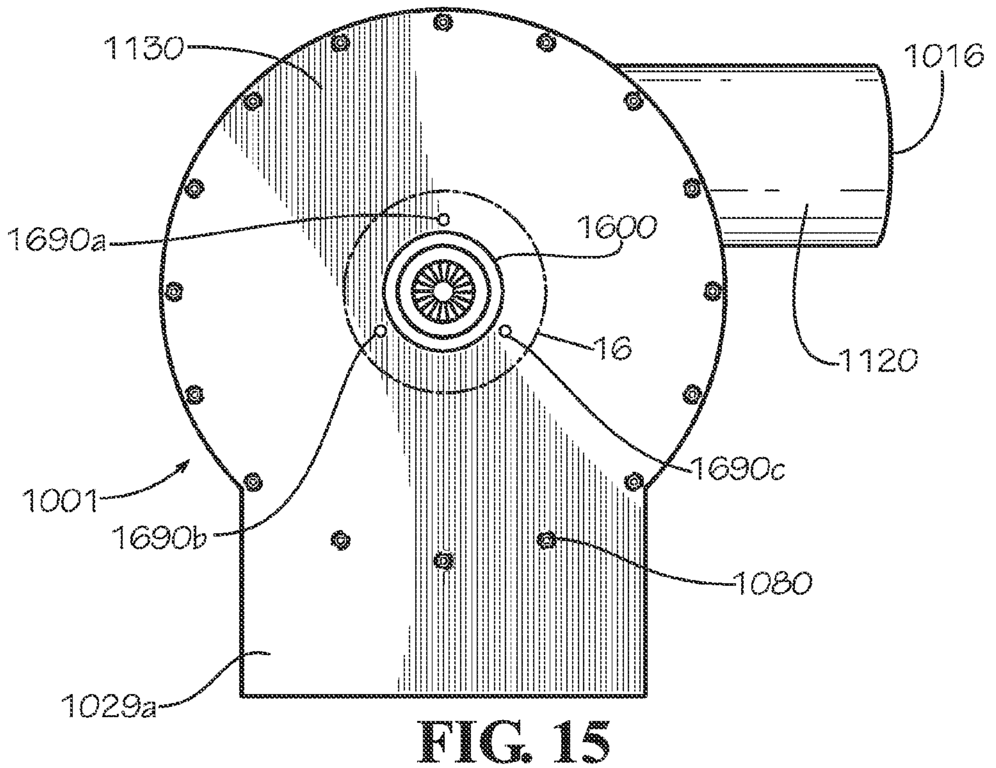
FIG. 15 is a perspective end view of an inlet side of the system of FIG. 10 with an inlet guard of the system removed.

FIG. 15 discloses in perspective view an inlet side of the dryer 1001 showing the acoustic head 1600 in place but without an inlet guard such as the inlet guard 1040. The end plate 1130 of the acoustic chest 1004 of the dryer 1001 defines three attachment holes 1690*a,b,c*, which are threaded to match the fasteners 1290 (shown in FIG. 10), to secure the inlet guard 1040 (shown in FIG. 10) in various embodiments. The fasteners 1080 are arranged in a circular pattern in various embodiments and line up with a first axial end of the body 1110 in which threaded holes (not shown) are defined to accept the fasteners 1080.

Figure 16:
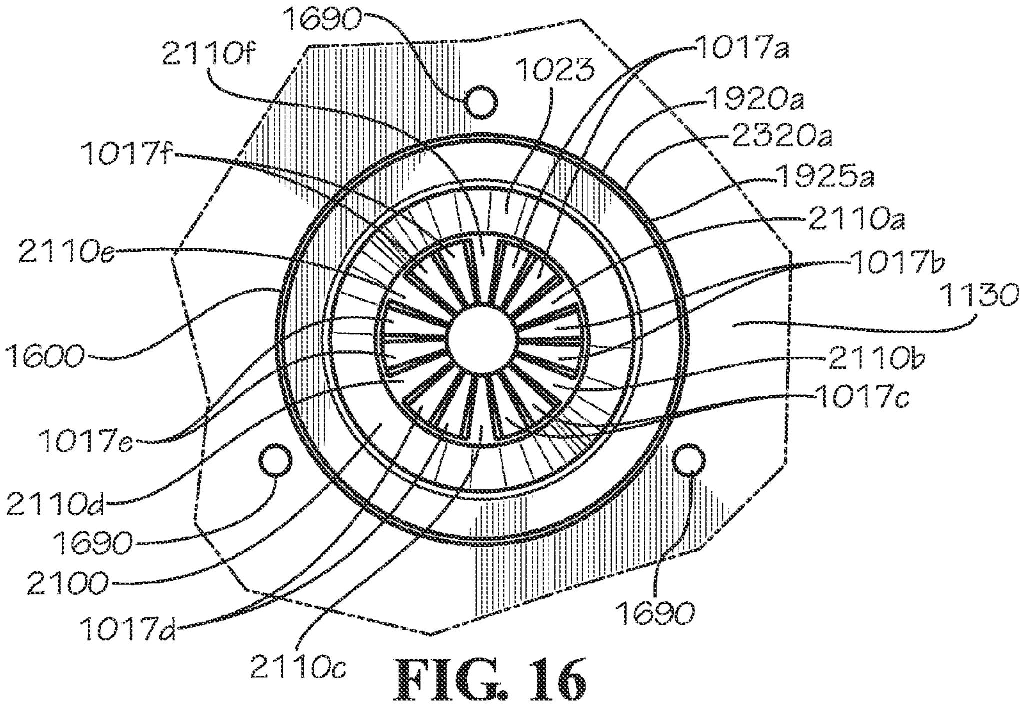
FIG. 16 is a detail perspective view of the inlet side of FIG. 15 taken from detail 16 of FIG. 15.

FIG. 16 discloses in greater detail the same perspective view of the inlet side of the dryer 1001. In various embodiments, a transducer mount 2100 of the acoustic head 1600 defines the inner chamber 1023, and a plurality of ultrasonic transducers 1017*a,b,c,d,e,f* is assembled to the transducer mount 2100. Between each of the plurality of ultrasonic transducers 1017 in various embodiments is a mount rail 2110. In various embodiments, the transducer mount 2100 of the acoustic head 1600 includes a plurality of mount rails 2110*a,b,c,d,e,f*. Each of the ultrasonic transducers 1017 and the mount rails 2110 are disclosed in additional detail in subsequent figures including FIG. 21.

Figure 17:
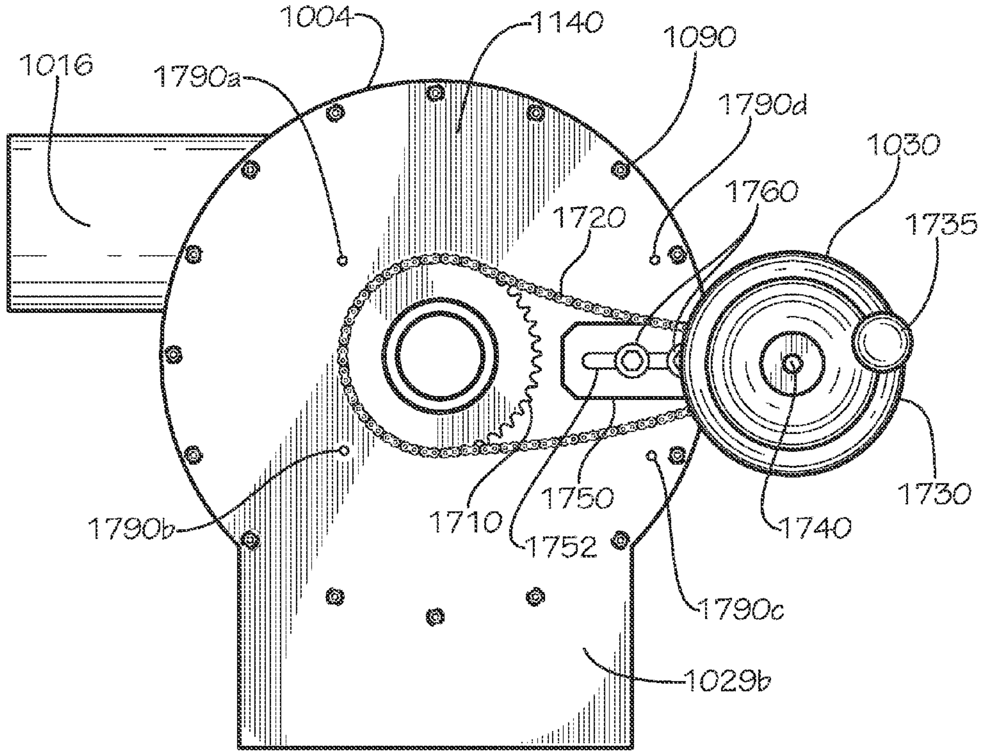
FIG. 17 is an end view of the outlet side of the system of FIG. 10 with an outlet guard of the system removed.

FIG. 17 discloses a perspective view of the outlet side of the dryer 1001 but without an outlet guard such as the outlet guard 1050. The end plate 1140 of the acoustic chest 1004 of the dryer 1001 defines four attachment holes 1790*a,b,c,d*, which are threaded to match the fasteners 1390 (shown in FIG. 11), to secure the outlet guard 1050 (shown in FIG. 11) in various embodiments. The fasteners 1090 are arranged in a circular pattern in various embodiments and line up with a second axial end of the body 1110 in which threaded holes (not shown) are defined to accept the fasteners 1090.

Figure 18:
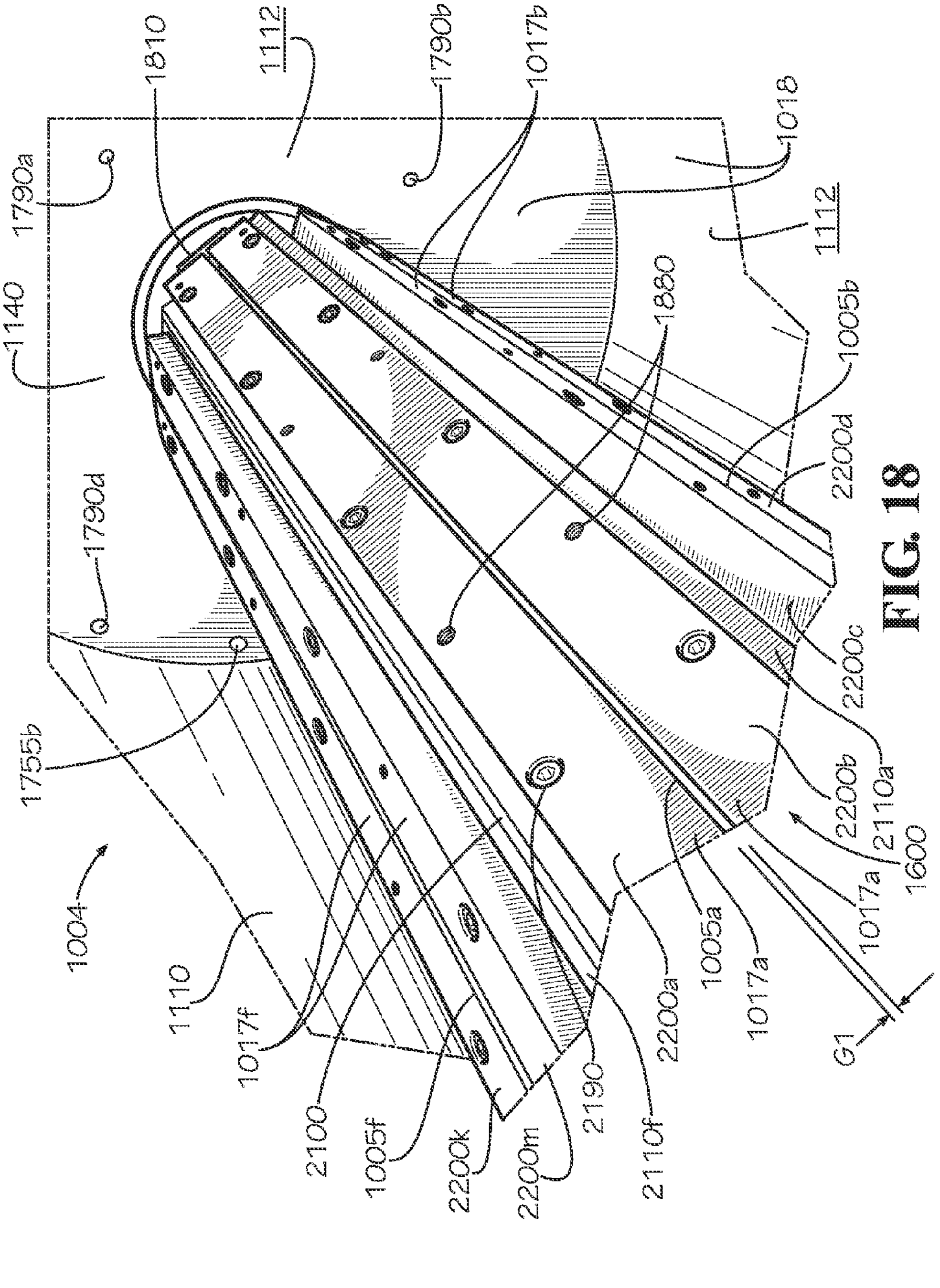
FIG. 18 is a perspective view of an interior of an acoustic chest of the system of FIG. 10 as viewed from the inside of the acoustic chest.

FIG. 17 additionally discloses the rotating drive mechanism 1030, which includes a working sprocket 1710, a chain 1720, a drive sprocket (not shown), a drive shaft 1740, and an adjustable attachment bracket 1750 held in position with fasteners 1760 assembled in attachment holes 1755*a,b* (1755*a* not shown, 1755*b* shown in FIG. 18). In various embodiments, the chain 1720 is a roller chain as shown and may also comply with the requirements for an ANSI chain No. 35. In various embodiments, the working sprocket 1710 has 30 teeth and is compatible with an ANSI chain No. 35 having a ⅜" pitch (see Part No. 2299K316 available from McMaster-Carr). In various embodiments, the drive sprocket has 9 teeth is compatible with an ANSI chain No. 35 having a ⅜" pitch (see Part No. 2299K316 available from McMaster-Carr). The attachment bracket 1750 includes an attachment cutout, which in the current embodiments is an adjustment slot 1752 that allows the position of the attachment bracket 1750 to be adjusted to achieve a desired tension in the chain 1720.

In various embodiments, the rotating drive mechanism 1030 also includes a wheel 1730 attached to the drive shaft 1740 and a grip 1735 attached to the wheel 1730. The disclosure of an acoustic energy-transfer system 1000 containing a chain 1720 and sprockets for the rotating drive mechanism 1030 should not be considering limiting on the current disclosure, however, as one may employ other means of rotating the acoustic head 1600 including, but not limited to, a belt and pulleys, a gearbox, and any one of a number of other systems for transmitting rotational movement. The disclosure of an acoustic energy-transfer system 1000 containing the wheel 1730 and the grip 1735 for supplying power to the rotating drive mechanism 1030 should not be considering limiting on the current disclosure, however, as one may employ other means of supplying power to the drive shaft including, but not limited to, a motor including a single-speed or a variable-speed motor, an engine, and any one of a number of other systems for providing power. In various embodiments, the rotating drive mechanism 1030 may include idler gears or rollers and may include a system for varying the speed by methods including, but not limited to, mechanical derailleurs and electronic motor control.

FIG. 18 discloses a perspective view of the inside of the acoustic chest 1004 when viewed alongside the acoustic head 1600 facing an inside surface of the end plate 1140. The acoustic chest 1004 is shown with the container wall 1018 defining the inner surface 1112 and with the inner surface 1112 defining the attachment holes 1790*a,b,d* and the attachment hole 1755*b*. The acoustic head 1600 is shown with the ultrasonic transducers 1017*a,b,f* defining a plurality of acoustic slots 1005*a,b,f*, respectively.

In various embodiments, each of a pair of end caps 1810 includes a pair of attachment holes (not shown), through which a pair of fasteners (not shown) may be used to cover or close a gap G1 between each pair of transducer bars 2200 of each ultrasonic transducer 1017 and to maintain the desired spacing therebetween. In various embodiments, the gap G1 is constant along the entire length of each ultrasonic transducer 1017. In various other embodiments, the gap G1 widens or narrows or varies in a non-linear fashion along the length of each ultrasonic transducer 1017 to produce acoustically energized air 1007 (shown in FIG. 21) that varies in it characteristics over the length of the dryer 1001. In various embodiments, the transducer mount 2100 is exposed between pairs of adjacent ultrasonic transducers 1017. In the current embodiment, for example, the mount rail 2110*a* of the transducer mount 2100 is exposed between the ultrasonic transducer 1017*a* and the ultrasonic transducer 1017*b*, and the mount rail 2110*f* of the transducer mount 2100 is exposed between the ultrasonic transducer 1017*a* and the ultrasonic transducer 1017*f*. In various embodiments, the ultrasonic transducers 1017 define a plurality of holes 1880 for attachment of a cover or other accessories onto one or more of ultrasonic transducers 1017.

Figure 19:
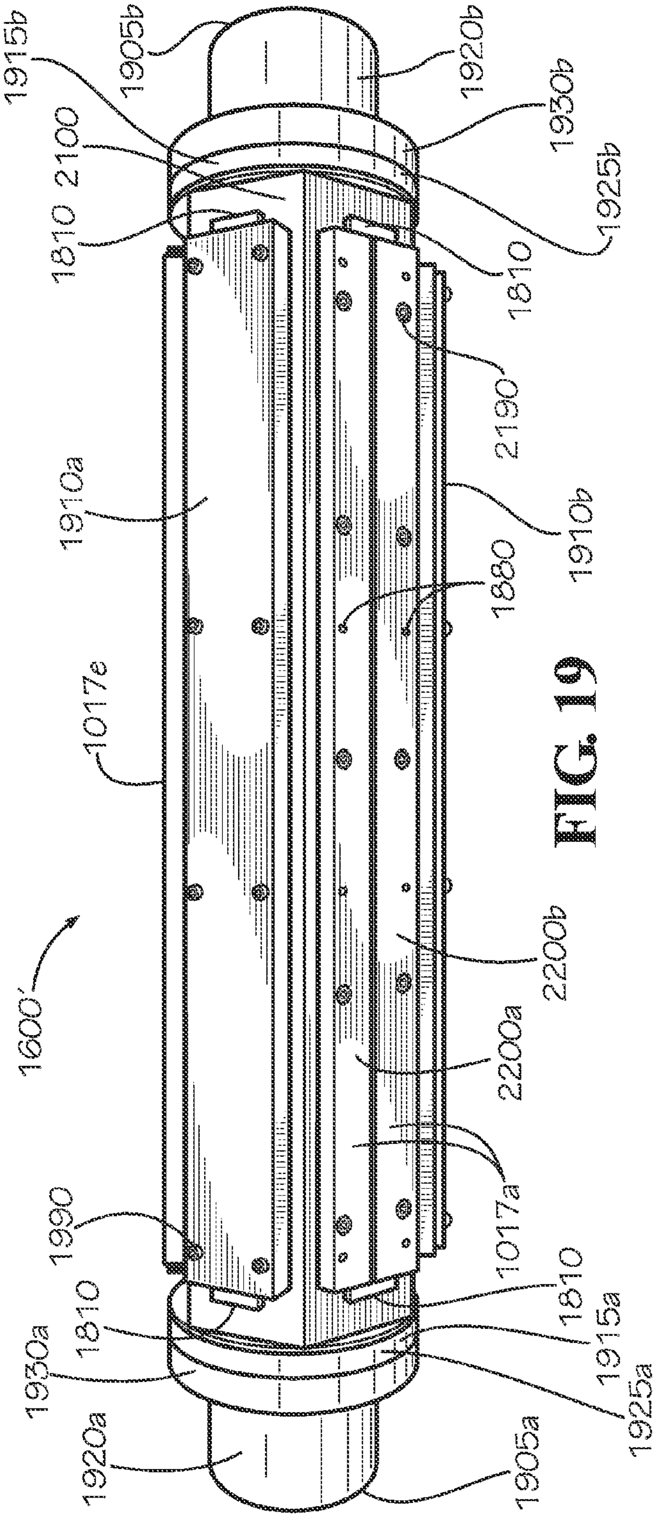
FIG. 19 is a perspective side view of an acoustic head of the system of FIG. 10 in accordance with another embodiment of the current disclosure.

FIG. 19 discloses an acoustic head 1600' without the surrounding components of an acoustic energy-transfer system such as the acoustic energy-transfer system 1000. The acoustic head 1600' includes the transducer mount 2100 and the ultrasonic transducers 1017*a,b,c,d,e,f*; however, the alternating ultrasonic transducers 1017*b,d,f* are covered with covers 1910*a,b,c* (1910*c* not shown), respectively, that result in acoustically energized air such as acoustically energized air 1007 being discharged from only the uncovered ultrasonic transducers 1017*a,c,e*. By selectively covering one or more of the ultrasonic transducers 1017, the number of acoustic slots 1005 is reduced. In various embodiments, covering one or more of the ultrasonic transducers 1017 has the effect of reducing the volume of acoustically energized air 1007. In various embodiments, each cover 1910 is secured to matching ultrasonic transducers 1017 with fasteners 1990.

In the area of the transducer mount 2100 where the ultrasonic transducers 1017 are attached, the transducer mount 2100 defines a substantially hexagonal cross-section. Axially beyond the area of the transducer mount 2100 having a substantially hexagonal cross-section and proximate a pair of ends 1905*a,b*, the transducer mount includes a pair of shaft end fittings 1925*a,b*. In various embodiments, the shaft end fittings 1925*a,b* include a pair of shoulder portions 1915*a,b*, respectively, each having a circular cross-section. Extending from the shoulder portion 1915*a* of the transducer mount 2100 towards the end 1905*a* is a bearing portion 1920*a*, which itself has a substantially circular cross-section. Extending from the shoulder portion 1915*b* of the transducer mount 2100 towards the end 1905*b* is a bearing portion 1920*b*, which itself also has a substantially circular cross-section. In various embodiments, an outer diameter of each of the shoulders portions 1915*a,b* is greater than an outer diameter of each of the bearing portions 1920*a,b*.

Figure 20:
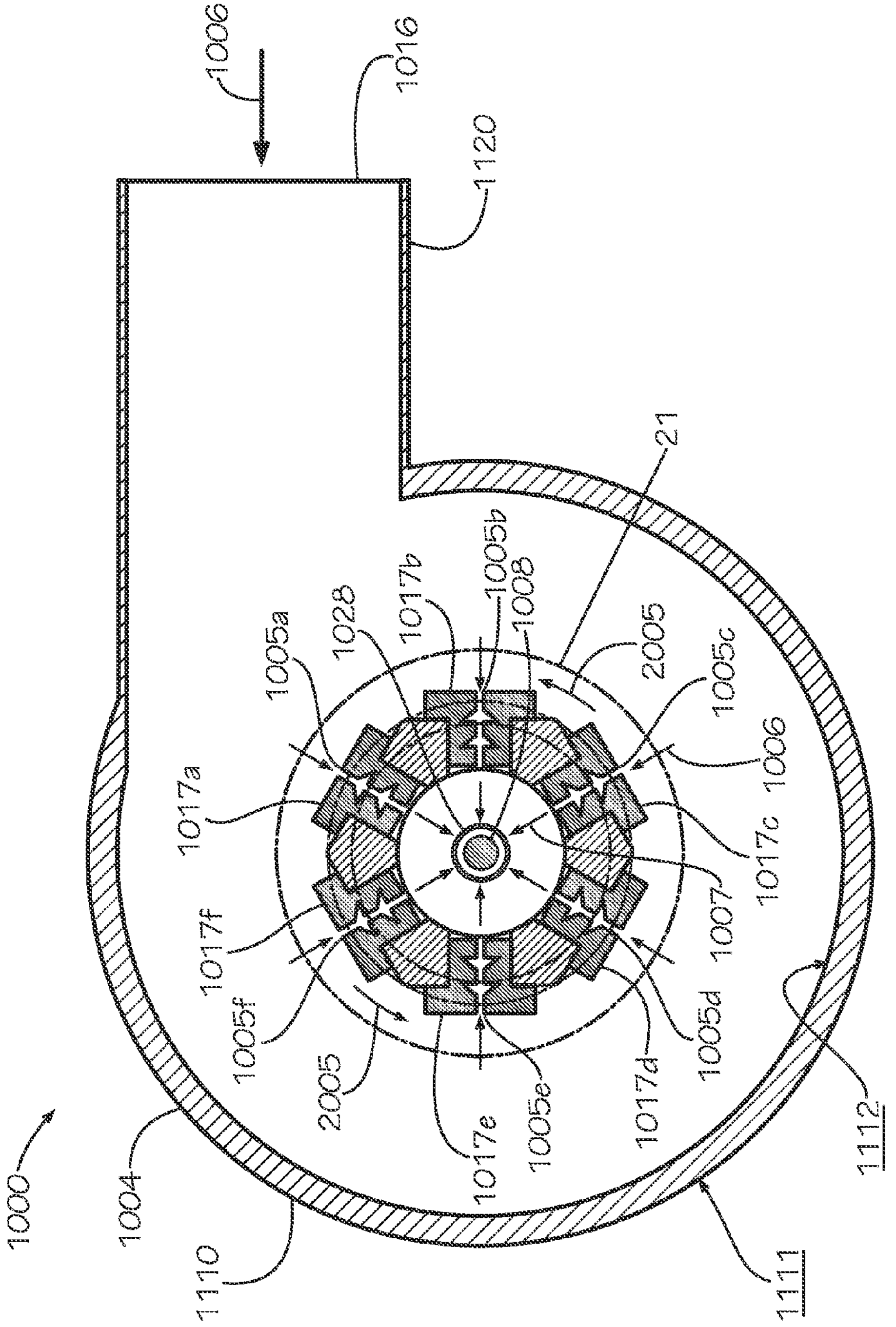
FIG. 20 is a sectional view of the system of FIG. 10 taken along lines 20-20 of FIG. 10 and showing only the geometry lying in a vertical plane represented by the lines 20-20 of FIG. 10.

FIG. 20 discloses a sectional view of the acoustic energy-transfer system 1000 taken in a vertical plane even with an axis of the inlet tube 1120 and facing the end plate 1140 but not showing any structures outside the vertical plane. The acoustic head 1600 is shown rotating in a rotational direction 2005 inside the acoustic chest 1004. The inlet air 1006 is shown entering each of the ultrasonic transducers 1017 and exiting each as the acoustically energized air 1007 and facing the material 1008 held in material support 1028. The disclosure of the rotational direction 2005 should not be considered limiting on the current disclosure, however, as the acoustic head 1600 in various embodiments may rotate in a direction opposite of the rotational direction 2005 or may oscillate between the rotational direction 2005 and a direction opposite the rotational direction 2005.

Figure 21:
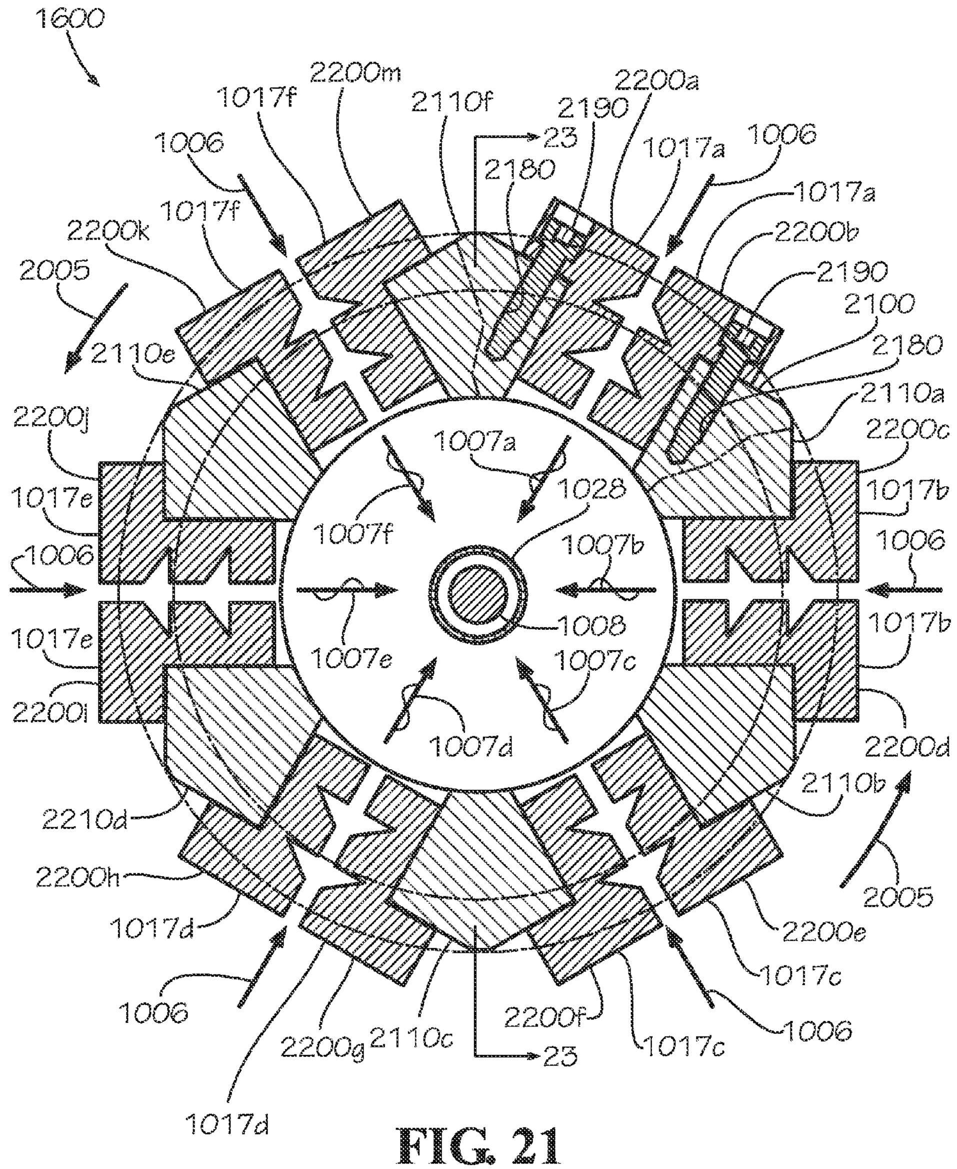
FIG. 21 is a detail sectional view of the acoustic head of the system of FIG. 10 taken from detail 21 of FIG. 20.

FIG. 21 is a detail sectional view of the acoustic head 1600, the material 1008, and the material support 1028 of the acoustic energy-transfer system 1000. The acoustic head 1600 is shown rotating in a rotational direction 2005. The inlet air 1006 is shown entering each of the ultrasonic transducers 1017*a,b,c,d,e,f* and exiting each as the acoustically energized air 1007*a,b,c,d,e,f*, respectively and facing the material 1008 held in material support 1028. In the current embodiment, the ultrasonic transducer 1017*a* includes the transducer bar 2200*a*, the transducer bar 2200*b*, and the two end caps 1810; the ultrasonic transducer 1017*b* includes a transducer bar 2200*c*, a transducer bar 2200*d*, and two more end caps 1810; the ultrasonic transducer 1017*c* includes a transducer bar 2200*e*, a transducer bar 2200*f*, and two more end caps 1810; the ultrasonic transducer 1017*d* includes a transducer bar 2200*g*, a transducer bar 2200*h*, and two end caps 1810; the ultrasonic transducer 1017*e* includes a transducer bar 2200*i*, a transducer bar 2200*j*, and two more end caps 1810; and the ultrasonic transducer 1017*f* includes a transducer bar 2200*k*, a transducer bar 2200*m*, and two more end caps 1810. The ultrasonic transducer 1017*a* is shown in a partial cutaway view at a point intersecting a pair of fasteners 2190 assembled in bores 2180 of the mount rails 2110*a,f* of the transducer mount 2100. In various embodiments, each of the ultrasonic transducers 1017 is assembled in a similar fashion to the transducer mount 2100. In various embodiments, the ultrasonic transducers 1017 encircle the material 1008.

Figure 22:
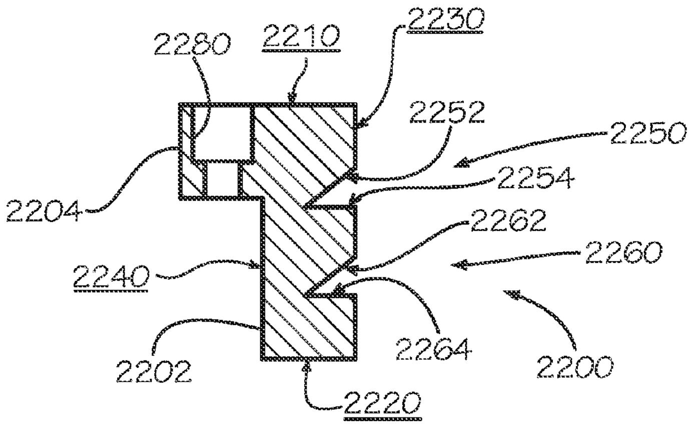
FIG. 22 is a detail sectional view of a transducer bar of an ultrasonic transducer of the acoustic head of FIG. 21.

FIG. 22 discloses a sectional view of a single transducer bar 2200 of an ultrasonic transducer 1017 of the dryer 1001. In various embodiments, the transducer bar 2200 includes a working portion 2202 and an attachment portion 2204. The attachment portion 2204 defines a plurality of attachment bores 2280, which are located at various points along the length of the transducer bar 2200 for attaching the transducer bar to the transducer mount 2100. The transducer bar 2200 also includes an upper surface 2210, a lower surface 2220, an inner surface 2230, and an outer surface 2240. In various embodiments, the inner surface 2230 is considered part of the working portion 2202 and defines a first groove 2250 and a second groove 2260 for inducing acoustic oscillations in the acoustically energized air 1007 (shown in FIG. 21). In various embodiments, the first groove 2250 includes an angled portion 2252 that is angled with respect to the flow of air through the ultrasonic transducer 1017 and a flat portion 2254 that is orthogonal to the flow of air through the assembled ultrasonic transducer 1017. In various embodiments, the second groove 2260 includes an angled portion 2262 that is angled with respect to the flow of air through the ultrasonic transducer 1017 and a flat portion 2264 that is orthogonal to the flow of air through the assembled ultrasonic transducer 1017.

Figure 23:
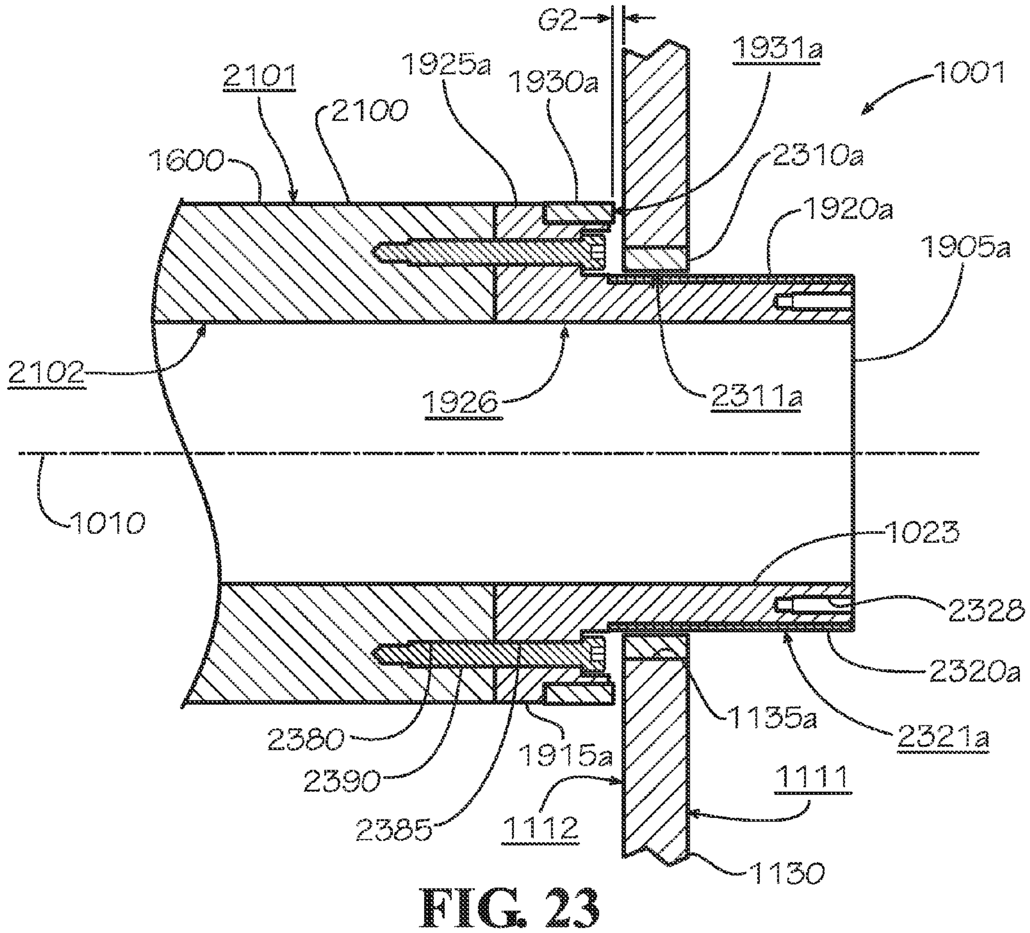
FIG. 23 is a sectional side view of the acoustic head of the system of FIG. 10 assembled in an end plate of the acoustic chest of the system of FIG. 10 taken along lines 23-23 of FIG. 21.

FIG. 23 is a sectional side view of the acoustic head 1600 as assembled in the end plate 1130 of the dryer 1001. The acoustic head 1600 includes the transducer mount 2100 and the pair of shaft end fittings 1925*a,b* assembled to the two ends of the transducer mount 2100. In various embodiments, the position of the shaft end fitting 1925*a* defines the end 1905*a* of the acoustic head 1600, and the position of the shaft end fitting 1925*b* defines the end 1905*b* of the acoustic head 1600. The transducer mount 2100 includes an outer surface 2101 and an inner surface 2102 and defines bores 2380 in each axial end sized to receive fasteners 2390 for assembling each shaft end fitting 1925 to the transducer mount 2100. In various embodiments, the shaft end fitting defines an inner surface 1926. In various embodiments, the shaft end fittings 1925*a,b* define one or more bores 2328 for securing accessories (not shown) to one or both ends of the acoustic head 1600.

In various embodiments, the shaft end fittings 1925*a,b* include shaft bushings 1930*a,b*, respectively (1930*b* shown in FIG. 19). In various embodiments, the shaft bushings 1930*a,b* fit within a stepped or rabbeted portion of the shaft end fittings 1925*a,b*, and in various embodiments an axial end surface 1931*a,b* of each shaft bushing 1930*a,b* is the facing surface of the acoustic head that is closest to the inner surface 1112 of the acoustic chest 1004. In various embodiments, the axial end surface 1931*a,b* of each shaft bushing 1930*a,b* is spaced away from the inner surface 1112 of the acoustic chest 1004 by a distance equal to the gap G2. In various embodiments, the shaft bushings 1930*a,b* are fabricated from brass and are assembled in bores 1135*a,b*, respectively, with a press-fit connection. The disclosure of brass for the shaft bushings 1930*a,b* and the disclosure of a press-fit connection, however, should not be considered limiting on the current disclosure.

In various embodiments, each of the end plates 1130,1140 includes one of a pair of plate bushings 2310*a,b*, respectively (2310*b* not shown). In various embodiments, the plate bushings 2310*a,b* fit within the bores 1135*a,b*, respectively (1135*b* not shown). In various embodiments, the plate bushings 2310*a,b* are fabricated from brass and are assembled in the bores 1135*a,b*, respectively, with a press-fit connection. The disclosure of brass for the plate bushings 2310*a,b* and the disclosure of a press-fit connection, however, should not be considered limiting on the current disclosure.

In various embodiments, the bearing portion 1920*a* includes an outer sleeve 2320*a*, and the bearing portion 1920*b* (shown in FIG. 19) includes an outer sleeve 2320*b* (not shown). In various embodiments, the outer sleeves 2320*a,b* (2320*b* not shown) fit on an outside surface of the bearing portions 1920*a,b*, respectively. In various embodiments, the outer sleeves 2320*a,b* are fabricated from stainless steel and are assembled on the bearing portions 1920*a,b*, respectively, with a press-fit connection. The disclosure of stainless steel for the outer sleeves 2320*a,b* and the disclosure of a press-fit connection, however, should not be considered limiting on the current disclosure. In various embodiments, an outer surface 2321 of the bearing portion 1920 comes into facing contact with an inner surface 2311 of the plate bushing 2310. In various embodiments, each bearing portion 1920 defines bores 2385 for receiving the fasteners 2390.

In various embodiments, the acoustic energy-transfer system 1000 includes the acoustic chest 1004, the acoustic chest 1004 defining a substantially enclosed cross-section and able to receive a material 1008 to be dried, cooled, or heated; and an acoustic slot 1005 defined within the acoustic chest 1004. In various embodiments, the acoustic chest 1004 defines a cylindrical cross-section. In various embodiments, the acoustic slot 1005 faces radially inward. In various embodiments, the ultrasonic transducer 1017 defines the acoustic slot 1005. In various embodiments, each of a plurality of ultrasonic transducers 1017 defines an acoustic slot 1005. In various embodiments, each of a plurality of ultrasonic transducers 1017 faces a central axis 1010 of a cylindrical cross-section of the acoustic chest 1004. In various embodiments, the ultrasonic transducer 1017 is assembled to the acoustic head 1600, the acoustic head 1600 rotatable about the central axis 1010 of the acoustic chest 1004. In various embodiments, the acoustic energy-transfer system 1000 further includes a drive mechanism for transporting the material 1008 through the dryer 1001 or the rotating drive mechanism 1030 for rotating the acoustic head 1600 about the material 1008, the rotating drive mechanism 1030 coupled to the acoustic head 1600 to rotate the acoustic head 1600 about the central axis 1010 of the acoustic chest 1004. In various embodiments, the central axis 1010 is a central axis of the acoustic head 1600. In various embodiments, an acoustic chest may have a central axis (not shown) that is not coincident with a central axis of the acoustic head 1600.

In various embodiments, the acoustic energy-transfer system 1000 includes the acoustic chest 1004; the ultrasonic transducer 1017 enclosed within the acoustic chest 1004; and the inner chamber 1023, the material 1008 receivable within the inner chamber 1023. In various embodiments, the acoustic chest 1004 defines a cylindrical cross-section. In various embodiments, an inner surface of the inner chamber 1023 defines a polygonal cross-section. In various embodiments, the acoustic energy-transfer system 1000 further includes the material 1008, the material 1008 enclosed within the inner chamber 1023. In various embodiments, the acoustic energy-transfer system 1000 further includes the material support 1028 sized to receive and enclose the material 1008. In various embodiments, the acoustic energy-transfer system 1000 further includes the plurality of ultrasonic transducers 1017, each ultrasonic transducer 1017 defining the acoustic slot 1005. In various embodiments, the inner chamber 1023 defines an inner diameter (not shown) measuring 1.63 inches (4.14 cm). The disclosure of any particular measurement for the inner diameter of the inner chamber 1023 should not be considered limiting on the current disclosure, however, as the inner diameter of the inner chamber 1023 may be less than or greater than 1.63 inches. In various embodiments, a spaced distance between one or more acoustic slots 1005 and the material 1008 is selected such that an amplitude of the acoustic oscillations at the center of the material 1008 or at the surface of the material 1008 is maximized (see, e.g., U.S. Pat. No. 9,068,775 to Plavnik).

In various embodiments, a method for drying the material 1008 includes: positioning an ultrasonic transducer 1017 a spaced distance from the material 1008, the ultrasonic transducer 1017 defined in the inner chamber 1023 of the acoustic chest 1004 and the material 1008 enclosed within the acoustic chest 1004; forcing the inlet air 1006 through the ultrasonic transducer 1017; inducing acoustic oscillations in the ultrasonic transducer 1017 to produce the acoustically energized air 1007; and directing the acoustically energized air 1007 towards the material 1008. In various embodiments, the method includes rotating the ultrasonic transducer 1017 about the material 1008. In various embodiments, the method includes positioning each of the plurality of ultrasonic transducers 1017 a spaced distance from the material 1008, each of the plurality of ultrasonic transducers 1017 spaced a substantially equal distance from the material 1008. In various embodiments, the method further includes transporting the material 1008 through the inner chamber 1023 of the acoustic chest 1004. In various embodiments, the method further includes supporting the material 1008 with the material support 1028, the material 1008 enclosed within the material support 1028. In various embodiments, the material support 1028 is perforated.

Description of FIGS. 24A-25C and Related Embodiments

Oscillating radial tubular dryer or chiller.

In another embodiment, as shown in FIGS. 24A-25C, the acoustic slots may be arranged longitudinally along and at a radial distance away from the material. The material may then be passed through the middle of an oscillating dryer. Like in the acoustic energy-transfer system 900 shown in FIG. 9, objects or materials such as ropes, yarns, and the like may be dried or chilled using such a device.

Disclosed below is a list of the systems, components, or features or components shown in FIGS. 24A-25C as designated by reference characters.

Figure 24A:
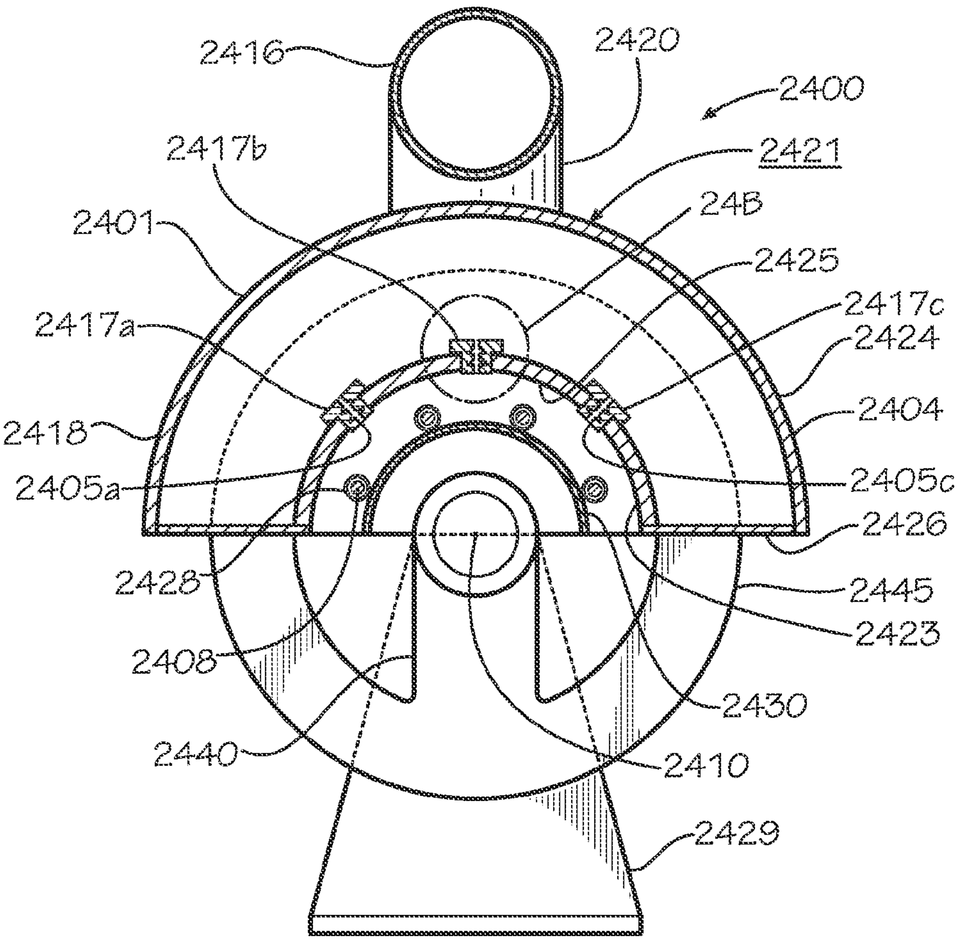
FIG. 24A is a sectional view of a cylindrical acoustic energy-transfer system in accordance with another embodiment of the current disclosure.

2400 acoustic energy-transfer system
2401 dryer
2404 acoustic chest
2405 acoustic slot
2406 inlet air
2407 acoustically energized air
2408 material (to be dried)
2410 central axis
2416 air inlet
2417 ultrasonic transducer
2418 container wall
2420 inlet tube
2421 outer surface
2423 inner chamber
2424 outer wall
2425 inner wall
2426 lower wall
2428 material support
2429 dryer support
2430 material support frame
2440 acoustic chest support frame
2445 support rim
2510 vertical axis
Θ rotation angle FIG. 24A discloses an acoustic energy-transfer system 2400 including an acoustic chest 2404 defining an inner chamber 2423 sized to receive a material 2408 for drying or cooling. In various embodiments, the acoustic chest 2404 forms a shape in cross-section that is substantially semicircular in shape. In various embodiments, the acoustic chest 2404 is rotatably assembled to a dryer support 2429 using an acoustic chest support frame 2440 having a support 2445 to which the acoustic chest is attached. In various embodiments, the acoustic chest is able to rotate or oscillate about a central axis 2410 to facilitate cooling of the material 2408.

In various embodiments, an inlet tube 2420 defining an air inlet 2416 is connected to an outer surface 2421 of the acoustic chest 2404. In various embodiments, the acoustic chest 2404 includes an outer wall 2424, an inner wall 2425 defining the inner chamber 2423, a lower wall 2426, and a plurality of acoustic slots 2405*a,b,c* (2405*b* shown in FIG. 24B). In various embodiments, each of a plurality of ultrasonic transducers 2417*a,b,c* of the acoustic chest 2404 defines each acoustic slot 2405.

Figure 24B:
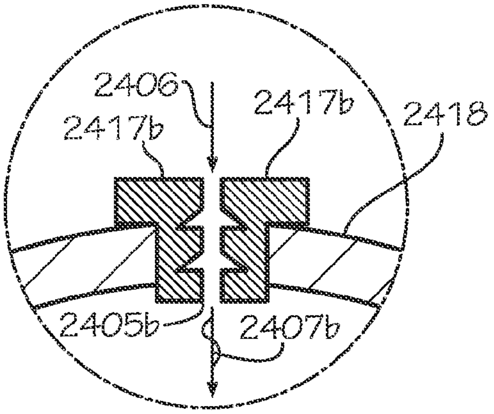
FIG. 24B is a detail sectional view of an acoustic device of the system of FIG. 24A taken from detail 24B of FIG. 24A.

FIG. 24B discloses the structure and operation of the acoustic slots 2405*a,b,c*. At the acoustic slots 2405*a,b,c*, the ultrasonic transducers 2417*a,b,c*, respectively, induce acoustic oscillations in the inlet air 2406 so as to create acoustically energized air 2407. In various embodiments, the material is stationary inside the dryer 2401 during the drying process. In various other embodiments, the material 2408 is made to pass through the acoustically energized air 2407 by transporting the material 2408 using a transport mechanism (not shown) in a transport direction (not shown) that is parallel to the orientation of the material 2408. In various embodiments, the ultrasonic transducers 2417*a,b,c* are oriented parallel to a central axis 2410 of the dryer 2401 in such a way that the path of the acoustically energized air 2407*a, b,c* (2407*a,c* not shown) coming straight out of the acoustic slots 2405*a,b,c* intersects the central axis 2410 of the dryer 2401.

In various embodiments, the air inlet 2416 delivers inlet air 2406 to the acoustic chest 2404 in the location shown at the top of the acoustic chest 2404. In various other embodiments, the air inlet 2416 may deliver air to multiple portions of the acoustic chest 2404 and may do so simultaneously. In various embodiments, the material 2408 to be cooled is transported through an inner chamber 2423 defined by a chamber wall 2418 of the acoustic chest 2404. The material 2408 may be transported from a material inlet (not shown) of the dryer 2401 to a material outlet (not shown) distal the material inlet in one transport direction parallel to the central axis 2410, or the material 2408 may be transported in an opposite direction. The material 2408 may also be transported along a conveyor (not shown) traveling along an upper surface of the material support frame 2430 or replacing the material support frame 2430. In various embodiments, the dryer 2401 also includes a material support 2428, which may be identical to the material support 1028 in various embodiments and which performs the function of supporting and maintaining the position of the material 2408. In various embodiments, the dryer 2401 includes a plurality of material supports 2428. The material supports 2428 may be attached to a material support frame 2430, which supports and maintains the position of the material supports 2428. In various embodiments, the material support frame 2430 is semicircular in shape to match the semicircular shape of the inner chamber 2423 and thus maintain the inner chamber 2423 a constant distance from the materials 2408.

In various embodiments, the material support 2428 is constant in cross-section and defines an inlet, an outlet, an outer surface, an inner surface, an inner diameter, and a length (none shown) sized to receive a variety of materials to be dried and cooled or heated such as the material 2408. In various embodiments, the material support 2428 resembles a pipe or tube as shown and has a cylindrical or other polygonal cross-section. The material support 2428 is a pre-punched spiral-wound and spiral-welded pipe with a seam (not shown) in the current embodiment. The material support 2428, however, may be formed or fabricated from any one or more of a variety of methods including, but not limited to, spiral winding and welding from plate, rolling and welding from plate, extruding, casting, and molding. The material support 2428 is fabricated from stainless steel in the current embodiment. The material support 2428, however, may be formed or fabricated from any one or more of a variety of materials including, but not limited to, steel including grades other than stainless steel, other metals, ceramics, polymers, or paper.

The material support 2428 defines a plurality of holes (not shown), which are circular in the current embodiment and facilitate passage of the acoustically energized air 2407 to any material 2408 enclosed within the material support 2428. The disclosure of a plurality of holes, which are circular in shape, should not be considered limiting on the current disclosure, however, as the material support 2428 may define openings that differ in shape from the holes that are shown. In various embodiments, the material support 2428 is able to not only support the weight of whatever material is enclosed thereby and dried by the dryer 2401, but the material support 2428 is also able to withstand the temperature extremes, the abrasion loads, and other stresses encountered during operation of the dryer 2401. In various embodiments the inlet or the outlet or both are cone shaped or fit with rollers to guide the material 2408 into the material support 2428. In various embodiments, the inner surface or the outer surface is fabricated in a way that eliminates any burrs or other impediments to the smooth movement of the material 2408 inside the material support 2428 during either loading of the material 2408 or during drying of loaded material 2408.

Figures 25A, 25B, 25C:
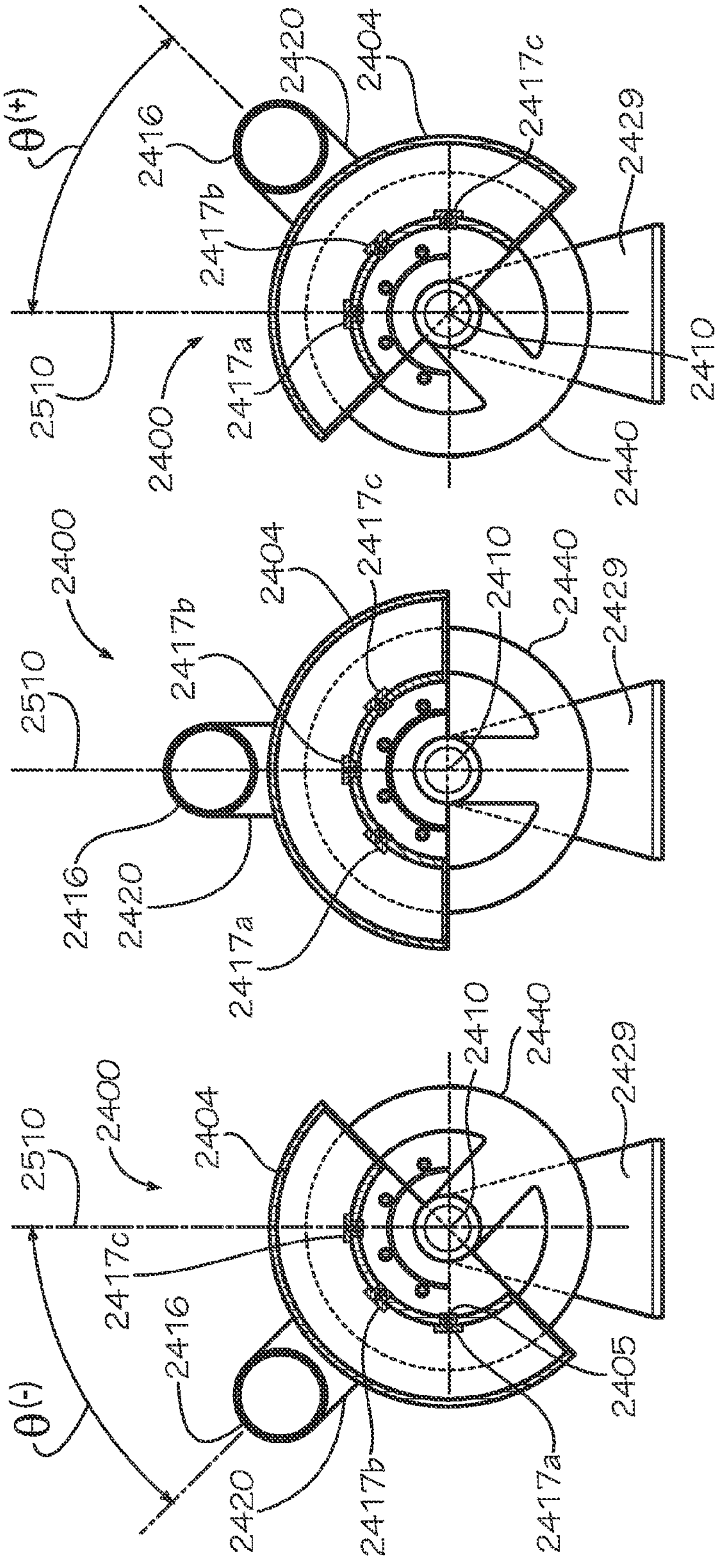
FIG. 25A is a sectional view of a first operating position of the system of FIG. 24A.
FIG. 25B is a sectional view of a second operating position of the system of FIG. 24A.
FIG. 25C is a sectional view of a third operating position of the system of FIG. 24A.

FIG. 25A is an end view of a first operating position or left operating position of the acoustic energy-transfer system 2400. When in the first operating position, the acoustic chest has rotated in a counterclockwise direction about the central axis 2410 a rotation angle Θ of 30 to 45 degrees or more until a right or first side of the acoustic chest 2404—and a center of the ultrasonic transducer 2417*c*—is aligned along a vertical axis 2510. In the current embodiment, the rotation angle Θ is approximately minus 45 degrees.

FIG. 25B is an end view of a second operating position or "neutral" operating position of the acoustic energy-transfer system 2400. When in the neutral operating position, a center of the acoustic chest 2404—and a center of the ultrasonic transducer 2417*b*—is aligned along a vertical axis 2510.

FIG. 25C is an end view of a third operating position or right operating position of the acoustic energy-transfer system 2400. When in the third operating position, the acoustic chest has rotated in a clockwise direction about the central axis 2410 a rotation angle Θ of 30 to 45 degrees until a left or second side of the acoustic chest 2404—and a center of the ultrasonic transducer 2417*a*—is aligned along a vertical axis 2510. In the current embodiment, the rotation angle Θ is approximately plus 45 degrees.

In various embodiments, the acoustic energy-transfer system 2400 includes the dryer 2401 including the acoustic chest 2404 enclosing within the inner chamber 2423 the material 2408 to be dried, cooled, or heated. In various embodiments, the acoustic chest further defines an acoustic slot 2405 enclosed within the acoustic chest 2404. In various embodiments, the acoustic chest 2404 oscillates about a central axis 2410.

In various embodiments, the acoustic energy-transfer system 2400 dries the material 2408 by positioning at least one ultrasonic transducer 2417 a spaced distance from a material 2408, the ultrasonic transducer 2417 defined in an inner chamber 2423 of the acoustic chest 2404 and the material 2408 enclosed within the acoustic chest 2404; by forcing inlet air 2406 through the at least one ultrasonic transducer 2417; by inducing acoustic oscillations or acoustically energized air 2407 in the at least one ultrasonic transducer 2417; and by directing the acoustically energized air 2407 at the material 2408. In various embodiments, the method of drying the material 2408 further includes causing the acoustic chest 2404 to oscillate about a central axis and about the material 2408.

In various embodiments, one or more structural components of the systems described herein are fabricated from an aluminum alloy material and one or more of the bushings or sleeves described herein are fabricated from a brass or stainless steel material. In various embodiments, mating parts such as the plate bushing 2310 and the outer sleeve 2320 are made from dissimilar materials to reduce or eliminate the risk of seizing of parts at high temperatures due to mating materials having properties, including thermal expansion and hardness properties, that are undesirably similar in various embodiments. In various embodiments, a lubricant such as dry graphite may be applied to mating surfaces such as the inner surface 2311*a* of the plate bushing 2310 and the outer surface 2321*a*. The disclosure of dry graphite should not be considered limiting on the current disclosure, however, as other lubricants or lubricating coatings including, but not limited to, polytetrafluoroethylene (PTFE) may be used in various embodiments. In various embodiments, one or more structural components of the systems described herein are fabricated from a corrosion-resistant material. In various embodiments, one or more components are made from a non-metallic material. In various embodiments, one or more components are made from a food-grade material. The disclosure of any particular materials or material properties should not be considered limiting on the current disclosure, however, as any number of different materials including aluminum, steel, copper, and various alloys and non-metallic materials could be used to form or fabricate the components described herein.

For purposes of the current disclosure, a physical dimension of a part or a property of a material measuring X on a particular scale measures within a range between X plus an industry-standard upper tolerance for the specified measurement and X minus an industry-standard lower tolerance for the specified measurement. Because tolerances can vary between different components and between different embodiments, the tolerance for a particular measurement of a particular component of a particular system can fall within a range of tolerances.

One should note that conditional language, such as, among others, "can," "could," "might," or "may," unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more particular embodiments or that one or more particular embodiments necessarily include logic for deciding, with or without user input or prompting, whether these features, elements and/or steps are included or are to be performed in any particular embodiment.

It should be emphasized that the above-described embodiments are merely possible examples of implementations, merely set forth for a clear understanding of the principles of the present disclosure. Any process descriptions or blocks in flow diagrams should be understood as representing modules, segments, or portions of code which include one or more executable instructions for implementing specific logical functions or steps in the process, and alternate implementations are included in which functions may not be included or executed at all, may be executed out of order from that shown or discussed, including substantially concurrently or in reverse order, depending on the functionality involved, as would be understood by those reasonably skilled in the art of the present disclosure. Many variations and modifications may be made to the above-described embodiment(s) without departing substantially from the spirit and principles of the present disclosure. Further, the scope of the present disclosure is intended to cover any and all combinations and sub-combinations of all elements, features, and aspects discussed above, including not only various combinations of elements within each embodiment but combinations of elements between various embodiments. For example, any ultrasonic transducer such as the ultrasonic transducer 117 is understood to be incorporated into any other embodiment disclosed herein including, but not limited to, embodiments where the ultrasonic transducer 117 is not disclosed or where a ultrasonic transducer is disclosed in less detail. All such modifications and variations are intended to be included herein within the scope of the present disclosure, and all possible claims to individual aspects or combinations of elements or steps are intended to be supported by the present disclosure.

That which is claimed is:

1. An acoustic energy-transfer apparatus comprising:

a dryer comprising an acoustic chest, the acoustic chest defining an inner chamber sized to receive a material to be processed, the acoustic chest defining a material inlet and a material outlet and a material path extending from the material inlet to the material outlet; and an acoustic device positioned within the acoustic chest, configured to rotate around the material path, and oriented to direct acoustic energy towards the material to be processed.

2. The apparatus of claim 1, wherein the acoustic chest defines a cylindrical cross-section.

3. The apparatus of claim 2, wherein the acoustic device faces radially inward.

4. The apparatus of claim 1, wherein the acoustic device is an ultrasonic transducer, the ultrasonic transducer defining an acoustic slot.

5. The apparatus of claim 1, further comprising a plurality of ultrasonic transducers within the acoustic chest, each ultrasonic transducer defining an acoustic slot.

6. The apparatus of claim 5, wherein the plurality of ultrasonic transducers are positioned to encircle the material to be processed.

7. The apparatus of claim 1, further comprising an acoustic head, the acoustic device assembled to the acoustic head, the acoustic head sized to receive the material to be processed.

8. The apparatus of claim 7, wherein the acoustic head is rotatable about the material to be processed.

9. The apparatus of claim 1, further comprising a rotating mechanism, the rotating mechanism coupled to the acoustic device to rotate the acoustic device about a central axis of an acoustic head including the acoustic device.

10. The apparatus of claim 1, wherein the material path is aligned with a central axis of the acoustic chest.

11. The apparatus of claim 10, wherein at least one of the material inlet and the material outlet define an air outlet.

12. The apparatus of claim 1, further comprising a material support for enclosing and supporting the material to be processed.

13. The apparatus of claim 12, wherein the material support is perforated.

14. The apparatus of claim 1, further comprising a material support, wherein the material to be processed is receivable within the material support.

15. A method for processing drying a material, the method comprising:

positioning a material in an acoustic chest of a dryer, the acoustic chest including an acoustic head defining a central axis, the acoustic head comprising a plurality of ultrasonic transducers, each of the ultrasonic transducers facing a central axis of the acoustic head;

rotating the acoustic head about the material within the acoustic chest; and directing acoustically energized air from the acoustic head at the material within the acoustic chest.

16. The method of claim 15, further comprising rotating the acoustic device about the material.

17. The method of claim 15, the method further comprising directing air through the plurality of ultrasonic transducers.

18. The method of claim 15, further comprising causing the material to move in an axial direction relative to an axial position of an inner chamber of the acoustic chest.

19. The method of claim 15, further comprising supporting the material with a material support, the material enclosed within the material support.

20. The method of claim 15, wherein the material being processed is left unsupported between a material inlet and a material outlet of the dryer.

* * * * *